United States Patent
Bai et al.

(10) Patent No.: US 8,178,721 B2
(45) Date of Patent: May 15, 2012

(54) PROCESSES FOR THE PRODUCTION OF L-CITRULLINE

(75) Inventors: Hua Bai, Taizhou (CN); Peijie Yang, Ningbo (CN); Zhengjie Chen, Taizhou (CN); Chongyang Xu, Taizhou (CN); Zhaorul Li, Taizhou (CN); Zigang Zhao, Taizhou (CN); Luyan Jiang, Taizhou (CN); Zongyi Yang, Taizhou (CN); Jiang Li, Taizhou (CN)

(73) Assignee: Global Strategic Connections, LLC, Troy, MI (US)

( * ) Notice: Subject to any disclaimer, the term of this patent is extended or adjusted under 35 U.S.C. 154(b) by 698 days.

(21) Appl. No.: 12/195,142

(22) Filed: Aug. 20, 2008
(Under 37 CFR 1.47)

(65) Prior Publication Data

US 2009/0142813 A1 Jun. 4, 2009

Related U.S. Application Data

(60) Provisional application No. 60/956,914, filed on Aug. 20, 2007.

(51) Int. Cl.
*C07C 227/00* (2006.01)
*C07C 273/00* (2006.01)

(52) U.S. Cl. .......................... 562/554; 562/560; 562/561

(58) Field of Classification Search ........................ None
See application file for complete search history.

(56) References Cited

U.S. PATENT DOCUMENTS 3,282,794 A * 11/1966 Okumura et al. ............. 435/114
3,886,040 A * 5/1975 Chibata et al. ................ 435/114

FOREIGN PATENT DOCUMENTS

GB 1176266 1/1970

OTHER PUBLICATIONS

Oreskes et al, Analytical Chemistry, Separation of Glutamine and Asparagine by Ion Exchange Chromatography with Temperature Programming, 1965, 37(13), pp. 1720-1723.*
International Search Report, Nov. 26, 2008, PCT/US2008/009926.

* cited by examiner

*Primary Examiner* — Paul A Zucker
(74) *Attorney, Agent, or Firm* — Young Basile

(57) ABSTRACT

Processes for producing a suitable purity grade of L-Citrulline are disclosed. The processes can include contacting crude L-Citrulline in an aqueous solution with an adsorptive medium at a temperature above approximately 50° C. and below the temperature of denaturement for the L-Citrulline for an interval sufficient to remove at least one contaminant from the L-Citrulline. The processes can also include concentrating the dissolved L-Citrulline relative to the aqueous solution.

10 Claims, 3 Drawing Sheets

PROCESSES FOR THE PRODUCTION OF L-CITRULLINE

RELATED APPLICATIONS

The presently disclosed subject matter claims the benefit of U.S. Provisional Patent Application Ser. No. 60/956,914, filed Aug. 20, 2007; the disclosure of which is incorporated herein by reference in its entirety.

TECHNICAL FIELD

The presently disclosed subject matter pertains to processes for producing purified L-Citrulline and products produced therefrom. More particularly, the presently disclosed subject matter pertains to processes for producing L-Citrulline suitable for use in pharmaceutical applications and material resulting from these processes.

BACKGROUND

The material L-Citrulline has been produced and used for various nutriceutical applications. Heretofore, its pharmacological applicability has been largely underappreciated. This is due, at least in part, to the cost and difficulty associated with producing L-Citrulline in a purity grade suitable for use in pharmacological applications. Possible end use applications include, but are not limited to, intravenous and subcutaneous infusion solutions, chewable dose forms, oral dose forms, sachet packaging, and suspensions.

SUMMARY

The present subject matter provided in some embodiments integrated processes for the production of unique forms of L-Citrulline of a type and grade suitable for use in pharmaceutical applications. The material can be present as crystalline material that can be further incorporated into suitable dose forms that include but are not limited to oral dose forms, sachet packaging suspensions and intravenous/subcutaneous solutions. In some embodiments of the methods disclosed herein, steps of production of L-Citrulline from various raw material such as a raw material grade of amino acids, for example, arginine, are provided. The resulting crystals possess unique characteristics and can be used in various pharmacological applications among other applications.

It is therefore an object of the present disclosure to provide novel processes for producing a suitable purity grade of L-Citrulline. An object having been stated hereinabove, and which is achieved in whole or in part by the subject matter disclosed herein, other objects will become evident as the description proceeds when taken in connection with the accompanying drawings as best described hereinbelow.

DETAILED DESCRIPTION

Reference will now be made in detail to the description of the present subject matter, one or more examples of which are shown in the figures. Each example is provided to explain the subject matter and not as a limitation. In fact, features illustrated or described as part of one embodiment can be used in another embodiment to yield still a further embodiment. It is intended that the present subject matter cover such modifications and variations.

As used herein, L-Citrulline and Citrulline are used interchangeably.

As used herein, "crude L-Citrulline" or "unrefined L-Citrulline" means any purity grade level of L-Citruiline below a grade level that is useable for the intended use of the L-Citrulline, including for example, but not limited to, a pharmacological use.

As used herein, "contaminant" includes discoloration media, endotoxin, pyrogen, and the like.

As used herein, "conversion material" means any material that is used as a material to be converted into L-Citrulline.

As used herein, "conversion solution" means any solution that contains a conversion material to be converted to L-Citrulline.

As used herein, "microbial," "microbial strain," "microbe," and "microbes" are used to reference any microorganism including, but not limited to, bacteria, fungi, archaea or protists that can be used to convert conversion material into L-Citrulline.

As used herein, "suitable purity grade" means any purity grade level of L-Citrulline that is substantially contaminant-free in some form or another. For example, in some embodiments, a suitable purity grade can be a purity grade level that is substantially endotoxin-free and/or pyrogen-free. For instance, in some embodiments, the L-Citrulline can have a suitable purity grade with a purity level of, for example, 99.7% contaminant free as measured by High Performance Liquid Chromatography ("HPLC").

As used herein "admixture" and "solution" and any variants thereof are used interchangeably.

Figure 1:
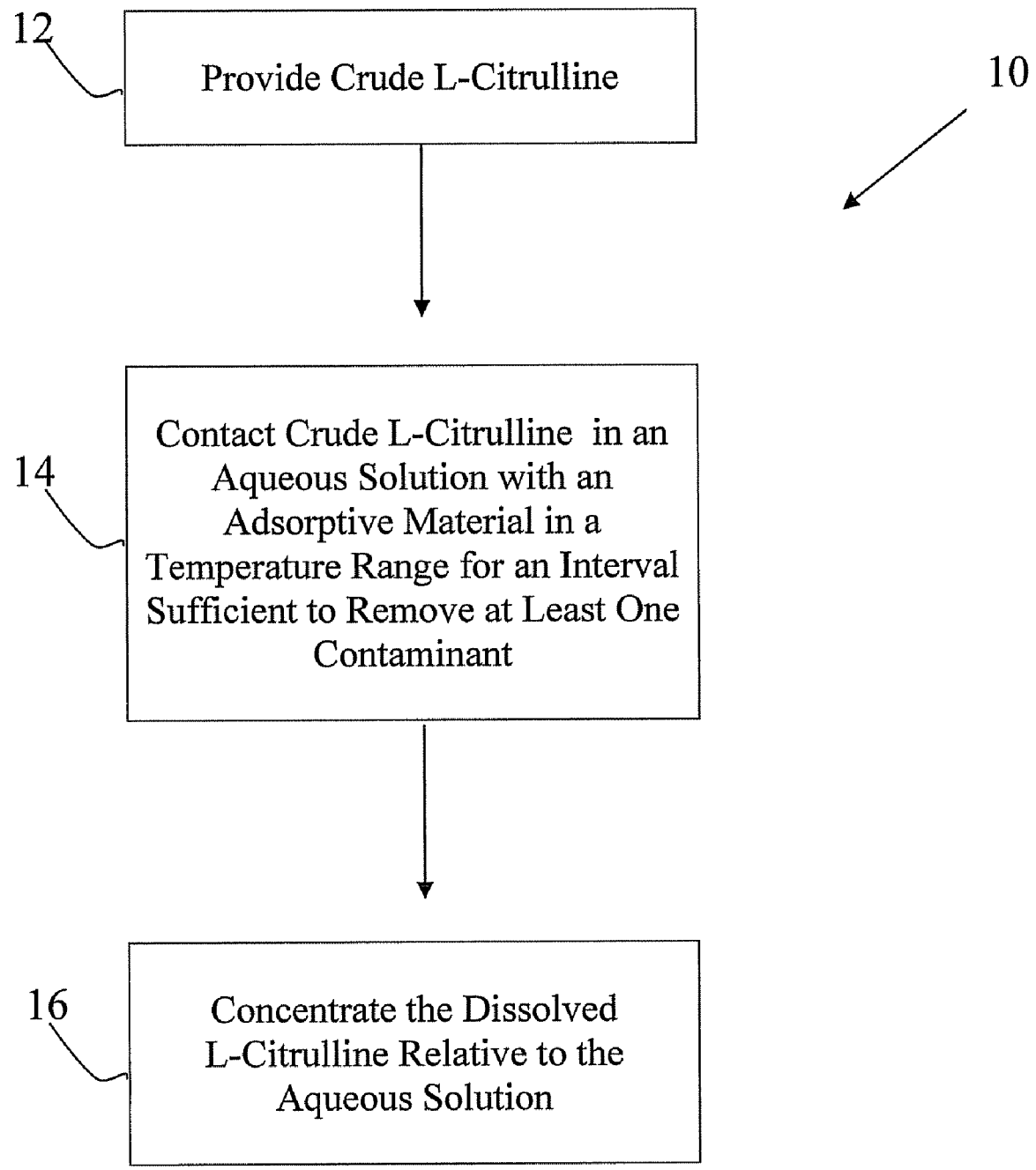
FIG. 1 is a flow chart illustrating steps of a method to produce purified L-Citrulline according to the present subject matter.

FIG. 1 illustrates a flowchart of steps in a method generally designated 10 of producing L-Citrulline in a purity grade suitable for pharmacological use. A first step 12 can include providing a crude or unrefined L-Citrulline material. L-Citrulline suitable for processing in the method disclosed herein can be obtained from a variety of sources. Various types or grades of L-Citrulline that are not at a purity level for pharmacological use can be processed using the methods disclosed herein to produce a purity grade level that permits pharmacological use. After processing, the resulting L-Citrulline material possesses one or more characteristics that render it pharmacologically useful and/or desirable.

Once a crude L-Citrulline material is provided in step 12, a step 14 can be performed of contacting the crude L-Citrulline in an aqueous solution with an adsorptive medium in a temperature range for an interval sufficient to remove at least one contaminant from the L-Citrulline. The adsorptive medium can be any type of adsorptive medium that can be used to purify the aqueous solution and the L-Citrulline by removing at least one contaminant therein. For example, the absorptive medium can comprise various forms of activated carbon can be the adsorptive medium.

In step 14, the temperature at which the crude L-Citrulline solution is maintained can be a temperature above approximately 50° C. and below the temperature of denaturement for the L-Citrulline. To maintain the temperature within the temperature range, heat can be applied as needed. The temperature can activate the adsorptive medium or at least increase the speed and/or effectiveness of its adsorptive characteristics. As described in more detail below, the temperature should stay below the temperature at which the L-Citrulline begins to denature.

After purification of the L-Citrulline containing aqueous solution by the removal of at least one contaminant, the L-Citrulline solution is concentrated in step 16. At this point, a more pure form of L-Citrulline can be provided. The purified L-Citrulline can have a purity level great enough for pharmacological use after this process. Alternatively, the purified L-Citrulline can still be too crude or unrefined for pharmacological use and can require further purification by repeating steps 14-16.

Figure 2:
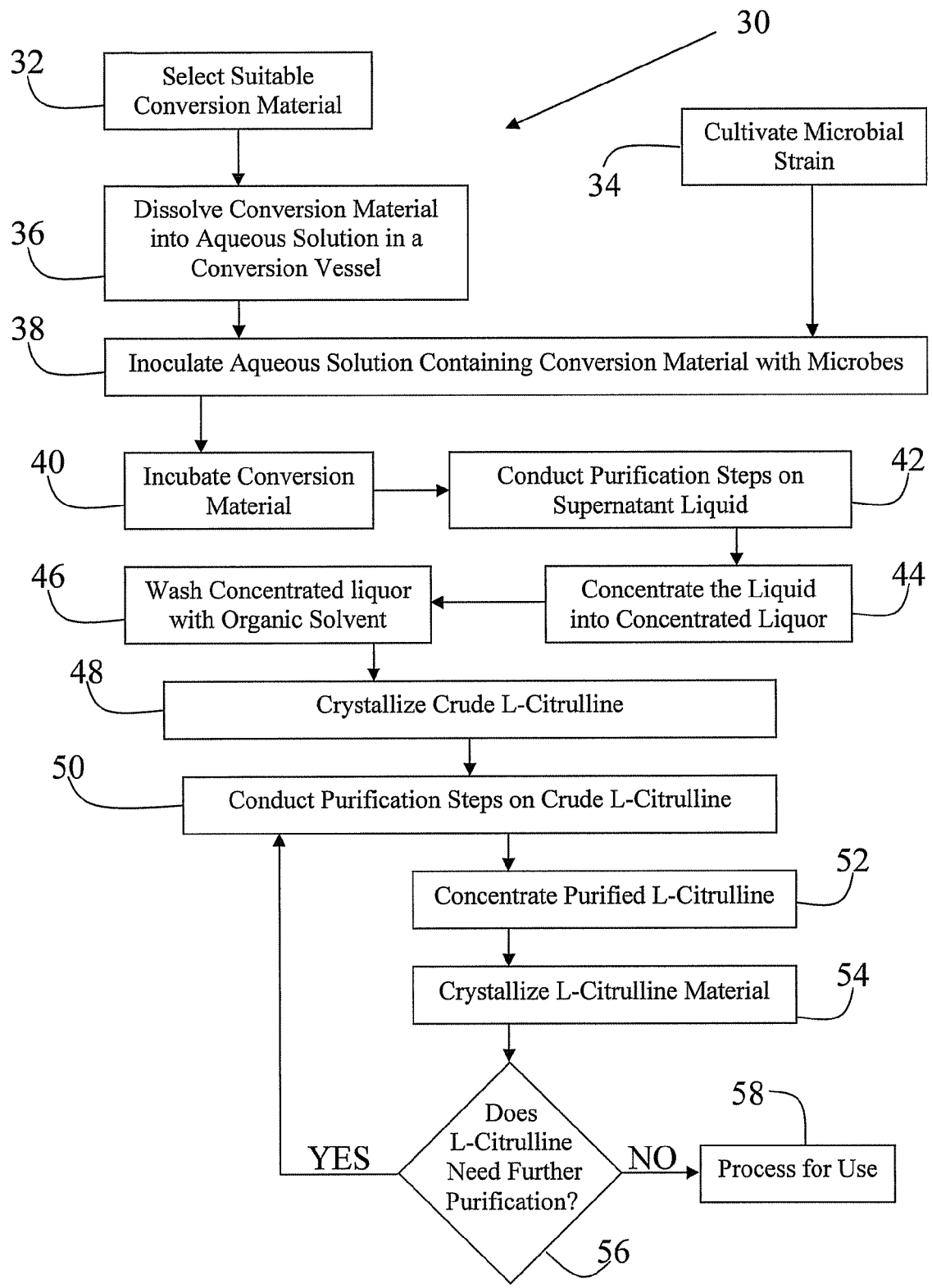
FIG. 2 is a flow chart illustrating steps of another method to produce purified L-Citrulline according to the present subject matter.

FIG. 2 illustrates a flowchart of another embodiment of a method generally designated 30 for producing L-Citrulline. Step 32 of selecting a suitable conversion material that can be used to provide L-Citrulline can be performed. As stated above, L-Citrulline can be obtained from a variety of sources. One suitable source utilizes the conversion of a suitable feedstock material to crude L-Citrulline in a suitable microbially mediated process such as fermentation. One non-limiting example of a suitable conversion material can be arginine. While the method disclosed herein encompasses any utilization of any form of arginine, the method can be employed with crude or unrefined arginine with suitable results. While the process disclosed herein is described in connection with L-Citrulline prepared from a fermentation process, it is provided that other types and sources of L-Citrulline can be employed where desired or feasible as in the embodiments described above.

Where the fermentation processes are employed to prepare or convert material into L-Citrulline, the process can proceed in the presence of a suitable microbial strain, for example, a bacteria such as *Faecalis streptococcic thalli*, seeded into a suitable incubation device such as a fermentor.

Thus, as shown in step 34, a suitable microbial strain can be cultivated by any suitable method. For example, a suitable microbial strain can be cultivated by inoculation into a suitable growth vessel such as a shaking flask with cultivation occurring during a suitable interval to produce seed stock. Cultivation can occur under conditions that promote microbial growth, for example, at standard temperature and pressure. Once seed material is produced, a portion of the seed material can be inoculated into a suitable fermentation to produce microbes suspended in a liquid media. The preparation of IV grade L-Citrulline or other pharmacological grade L-Citrulline disclosed herein can proceed from any suitable conversion material. Suitable non-limiting methods for producing L-Citrulline include various fermentation methods such as those outlined in U.S. Pat. No. 5,164,307, the specification of which is incorporated by reference herein in its entirety.

Once the microbial strain is cultivated, the cultivated microbes can be separated from the liquid media. Separation can be accomplished by any suitable method. For example, various centrifuge techniques can be employed to achieve separation and/or concentration of the microbes from or in the liquid media. Tube centrifugation is one method that can be employed with supernatant liquid being discarded as waste and the collected material being used to harvest an inoculant for subsequent process steps.

With reference to step 32, conversion material suitable for use in conversion to L-Citrulline can be any suitable material, for example, an amino acid. Arginine is one example of a suitable conversion material. In step 36, the suitable conversion material can be added to a suitable conversion vessel and dissolved in suitable aqueous medium to provide a conversion solution. The solution can also include suitable additives to support the conversion process.

The aqueous solution that acts as the conversion solution can have a pH suitable for supporting and promoting the conversion process. Where desired or required, the aqueous solution can be buffered to maintain the desired pH range. In conversion processes utilizing arginine, the conversion solution can have a slightly acidic pH. For example, a pH in a range of about 6.0 to about 6.7 can be desirable. Suitable buffers include but are not limited to dodecyl sulfate salts and the like.

Step 38 provides for inoculating the aqueous solution that contains conversion material with the microbes that have been cultivated and separated. For example, the solution charged with the conversion material such as arginine, other suitable amino acid or the like, can be inoculated with a suitable quantity of the microbial starter and permitted to react for an interval sufficient to trigger the conversion of the conversion material to crude L-Citrulline. Thus, after inoculation, step 40 of incubating the conversion material to L-Citrulline can occur. The conversion process will occur at a temperature to support the reaction. Typically, the reaction can occur at temperatures close to ambient. However, slightly elevated temperatures can be employed where desired or required. One non-limiting example of a suitable reaction temperature is incubation at about 37° C.

The incubation period can be sufficient to establish conversion of the material to L-Citrulline to a suitable degree of completeness. For example, the conversion can be from about 70% to about 100%, for instance from about 75% to about 95%. Suitable incubation periods can be from approximately 1 hour to over about 24 hours as desired or required. For example Faecalis *streptococcic thalli* mediated conversion of arginine to L-Citrulline can occur to a degree of completeness about 85% or greater, e.g., 86%, 87%, 88%, 89%, 90%, 91%, 92%, 93%, 94%, 95%, 96%, 97%, 98%, 99%, if conversion is permitted to proceed for an interval of about 20 hours at about 37° C. Once conversion is complete, the microbes can be separated from the supernatant liquid for reuse as required.

Where desired or required, incubation can occur with sufficient agitation to provide intimate contact between the microbes and the material to be converted. For example, stirring rates between about 100 and about 500 rpm can be employed.

The resulting supernatant liquid can be processed to produce crystalline L-Citrulline. In step 42, the supernatant liquid can under go purification steps as desired or required to remove discoloration and various impurities. Purification can occur by various methods including, but not limited to, filtration, adsorption, a combination of both filtration and adsorption and the like. For example, purification can be affected by admixture of the supernatant liquid with a suitable adsorptive medium. Non-limiting examples of suitable adsorptive medium includes various forms of activated carbon.

Contact can occur under conditions and for an interval sufficient to achieve suitable purification and/or decoloration. Thus, where desired or required, the material can be admixed with an adsorptive medium in a manner to ensure intimate contact such as by mechanical agitation or the like. While decoloring is discussed, it is considered to be within the purview of this disclosure to omit or truncate the decoloring step where desired or required.

Where desired or required, contact can occur at an elevated temperature to enhance contact and adsorptive activity. Elevated temperatures, where employed, can be capable of enhancing the adsorptive process but low enough to avoid any potential denaturing of the L-Citrulline material. Non-limiting examples of suitable temperature ranges include elevated temperatures between about 50° C. and about 80° C.

Contact between the adsorptive medium and the L-Citrulline material in the aqueous solution can proceed for an interval sufficient to achieve purification by removal of at least one contaminant from the L-Citrulline material. An interval of between about 30 minutes and about 3 hours can be sufficient in many instances after which the activated carbon can be removed from contact with the liquid.

In step 44, the resulting decolored L-Citrulline material can be concentrated by any suitable method. One non-limiting example of a suitable concentration method is low temperature vacuum distillation. The temperature of distillation is desirably lower than the temperature of denaturization of the L-Citrulline material. Non-limiting examples of suitable temperatures are between about 45° C. and about 85° C. For example, the temperature can range between about 50° C. and about 70° C. Suitable concentration ranges are concentrations greater that about 1:1. For example, a concentration ratio of about 3:1 can be provided. The concentration step 44 can thus create a concentrated liquor containing L-Citrulline material.

As outlined in step 46, the concentrated liquor can be washed with a suitable quantity of an organic liquid. For example, a water miscible organic solvent can be used, of which short chain alcohols are but one non-limiting example. The ratio of concentrated liquor to organic solvent can be selected that is suitable to depress the freezing point of the resulting liquid blend or admixture and dilute the aqueous component at a ratio of at least one to one; with organic to concentrate ratios of about 3:1 being provided in various instances.

In step 48, the L-Citrulline can be crystallized. For example, the L-Citrulline can be crystallized by cooling the L-Citrulline mixture for an interval sufficient to lower the temperature to a level sufficient to initiate crystal formation. For example, in various instances crystal formation can be triggered at temperatures below approximately 15° C. Where desired or required, the cooling can proceed with suitable stirring to promote crystal formation. The rate of temperature drop can be sufficient enough to achieve the desired formation of crystals from the solution.

Further, in step 48, the L-Citrulline crystals can be separated by any suitable method of which centrifugation is but one non-limiting example. The resulting material can be a crude L-Citrulline.

The resulting crude L-Citrulline crystals can be further processed in the manner disclosed herein. As described above with FIG. 1, the process disclosed can be utilized with crystalline L-Citrulline derived from other sources where desired or required depending upon the nature and characteristics of the resulting material.

In step 50, the crude L-Citrulline material can be subjected to at least one additional purification process. Purification can occur by various methods including, but not limited to, filtration, adsorption, a combination of both filtration and adsorption and the like. For example, the additional purification step can include, but need not be limited to, further dissolution in a suitable diluent. For instance, the diluent can be an aqueous medium such as deionized water. The aqueous medium can be passed through a filter or put in the presence of a suitable adsorptive medium, such as, but not limited to, about 1.0% activated carbon. The aqueous medium employed can be one that permits and facilitate dissolution and subsequent purification of the target material. The volume of the aqueous solution can be between about 1 and about 10 times the volume of the crude L-Citrulline with volumes between about 1 and about 2 times the volume of L-Citrulline being employed in certain situations.

In order to facilitate purification of the solution, the solution can be heated to a temperature below the temperature of denaturization of the L-Citrulline. Where heating is employed, solution temperatures in a range between about 45° C. and about 85° C. can be beneficial. The solution can also be stirred or otherwise agitated to promote contact between the solution and the adsorptive medium.

Contact between the solution and the adsorptive medium can proceed for an interval sufficient to achieve the desired level of purity. Contact in combination with heating and agitation can be for an interval between about 15 minutes and about 2 hours in certain situation.

In step 50, the resulting solution can be filtered to remove the adsorptive medium and any associated contaminants including, but not limited to endotoxin. Filtration can be accomplished by any suitable approach of which ultrafiltration with a suitable molecular weight membrane being but one example. Where desired or required, the solution can be separated from the associated adsorptive medium by other suitable methods.

In step 52, the filtrate solution containing the purified L-Citrulline is concentrated. The resulting filtrate solution can be concentrated by any suitable method. In the process disclosed herein, one suitable method is vacuum distillation at elevated temperature. Suitable temperatures are in the range capable of volatilizing the organic liquid without compromising the character or quality of the L-Citrulline contained therein. Suitable temperature ranges for at least some applications can be between about 65° C. and about 85° C. Concentration can proceed until a suitable ratio has been obtained. Concentration ratios between about 1:1 and about 4:1 from initial to final concentration levels are provided in representative embodiments.

The L-Citrulline material can then be crystallized in step 54. The resulting concentrated material can be allowed to cool gradually to a temperature that approximates ambient temperature after which the material can be further cooled to a solution temperature below crystal formation temperature. In certain instances, solution temperatures below about 15° C. are employed, with temperatures below about 5 to about 10° C. being employed in certain situations.

The material can be maintained at the depressed temperature for an interval sufficient to promote and achieve crystallization. Where desired or required, the crystallization process can proceed with suitable agitation to promote crystallization. Suitable intervals can be between about 30 minutes and about 3 hours depending upon specific characteristics of the material concentrate.

Further, in step 54, the crystallized material can be separated from the associated solution by any suitable separation method. Suitable separation methods include, but are not limited to, centrifugation methods such as bag centrifugation.

A determination can be made as to whether further processing can or should be performed in step 56. This determination can be decided before, during or after the previous steps. If further processing is desired, then the resulting material can be further processed in additional purification and recrystallization steps. In the repeat purification step, no adsorptive medium needs to be added. Instead, the purification process can be performed using increasingly fine filtration methods as desired or required to obtain a desired purity level of the L-Citrulline product. However, if necessary or beneficial, adsorptive medium can be used in this repeat purifying step.

In some embodiments, the recrystallized L-Citrulline material is subjected to at least one additional purification step and recrystallization step in which the second product of recrystallized L-Citrulline material is dissolved in a diluent. For example, the second product of recrystallized L-Citrulline material can be dissolved in deionized water at a ratio of about 1 to about 15 times the volume of the crystallized material and the resulting solution is filtered, such as with a 5K molecular weight membrane. The filtrate can be concentrated under vacuum at about 80° C. at a concentration rate of about 3:1 or other desired concentration ratio. The cool concentrated liquid can be cooled to about 5 to about 8° C., for example, and allowed to crystallize for about 1 hour, or other suitable or desired time.

The crystallized material is separated by a suitable separation technique. As discussed above, a non-limiting example of suitable separation method is a centrifugation method, such as bag centrifugation. If no further purifying and recrystallization is required and the appropriate purity grade level of the L-Citrulline has been obtained, then the L-Citrulline can be processed for use in step 58. For example, separation preformed by bag centrifugation produces a moist product that can be subsequently dried and packaged as a final product.

A more specific embodiment of a method generally designated 100 for producing L-Citrulline is described below.

1. Bacteria Strain and Fermentation Procedure

Figure 3:
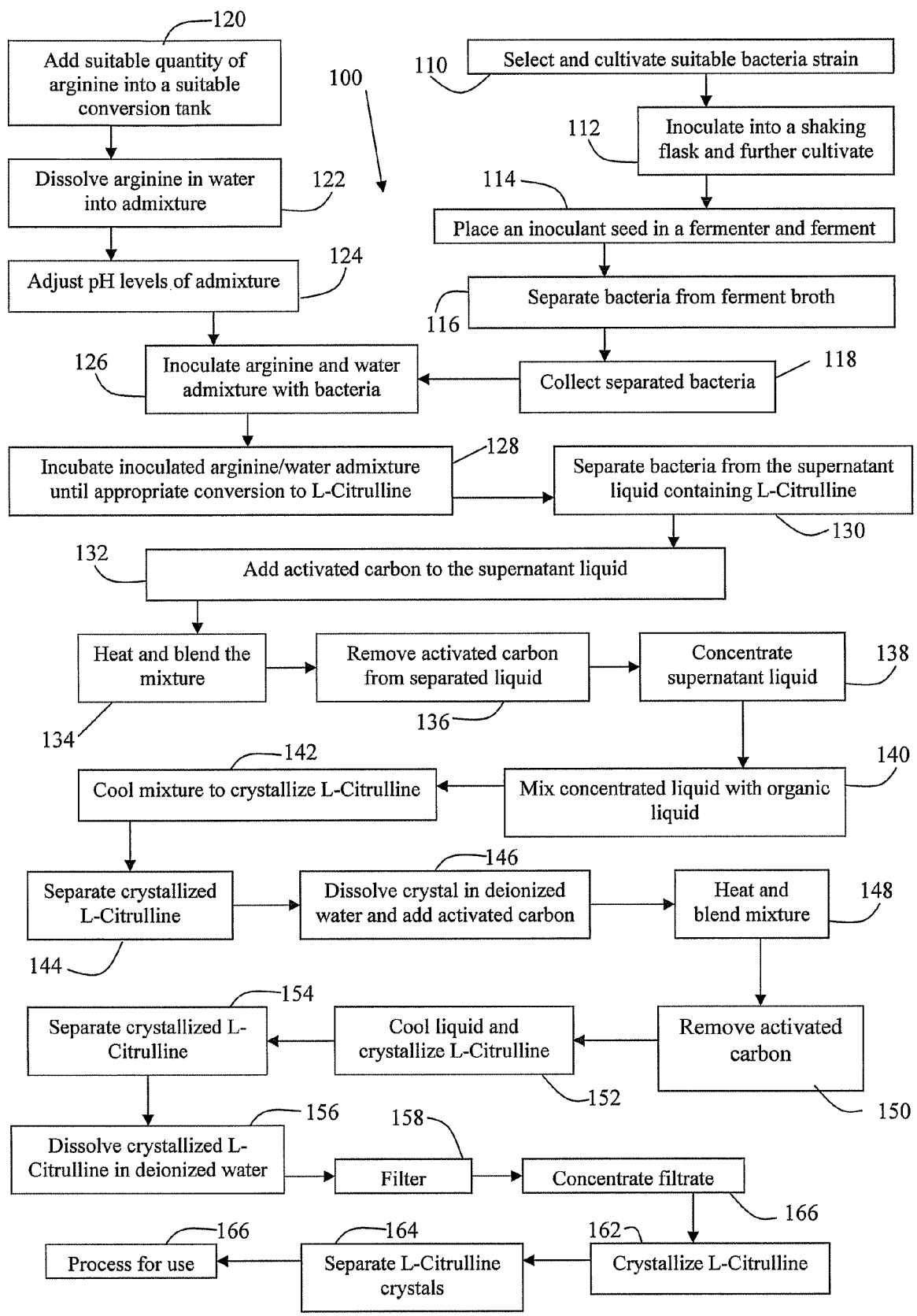
FIG. 3 is a flow chart illustrating steps of a further method to produce purified L-Citrulline according to the present subject matter.

Referring now to FIG. 3 in the method 100, before the production of L-Citrulline, a suitable bacteria strain such as *Faecalis streptococcic thalli* is selected and cultivated as in step 110. For example, the bacterial strain can be cultivated at about 37° C. for about 2 to 3 days. In step 112, the strain can be inoculated into a shaking flask and further cultivated at an appropriate temperature, a non-limiting example of which can be about 37° C. After cultivating further in the shaking flask for a suitable period such as about 18-22 hours, a fermentor can be seeded with inoculant in step 114. For example, an inoculant of about 1.0% of the seed can be introduced into a suitable fermentor. After cultivating for about 18-22 hours, fermentation can be terminated. In step 116, the bacteria can be separated from the supernatant liquid within the fermentation broth. The separation can be by a suitable method such as by centrifugation. One non-limiting example of a suitable separation technique includes tube centrifugation. The resulting supernatant liquid can be discarded as waste. The separated bacteria can then be collected in step 118. After collection, the separated bacteria can be used in the production of L-Citrulline.

2. Conversion Procedure

Continuing with FIG. 3, in step 120, a suitable quantity of arginine can be added into a suitable conversion tank or reaction vessel. In step 122, the arginine is dissolved in water in an admixture or conversion solution. The pH level of the conversion solution can be adjusted in step 124. The pH of the resulting conversion solution can be adjusted to a level of about 6.0 to about 7.0, for example, a pH range between about 6.0 and about 6.5, with a suitable inorganic acid such as HCl, and then buffered with a suitable buffer such as sodium dodecyl sulfate to maintain the pH of the conversion solution in the desired pH range. The arginine and water conversion admixture can then be inoculated with the collected bacteria as in step 126 to facilitate conversion of the arginine to L-Citrulline.

The collected bacteria, for example, *Faecalis streptococcic thalli*, can be added with conversion proceeding at a constant temperature of about +37° C. and with suitable agitation, for example, stirring at about 300 rpm. Incubation of the inoculated arginine and water conversion solution can then occur until appropriate conversion to L-Citrulline ensues as in step 128. After about 20 hours, the conversion solution can be sampled to test the extent of L-Citrulline conversion. If the extent of conversion is more than about 85%, the conversion reaction can be terminated and the bacteria separated from the conversion liquid as in step 130. The bacteria can be separated from the conversion liquid by a process such as tube centrifugation. The separated bacteria strain can be reused and the supernatant liquid containing the converted L-Citrulline sent to the next procedure.

3. Decolor and Crystallization Procedure

Continuing with FIG. 3, in step 132, an adsorptive medium can be added into the supernatant liquid containing the converted L-Citrulline. For example, about 1.0% activated carbon can be added into the supernatant liquid. The mixture can be heated to about 60-70° C. and blended in step 134. The heating and blending of the mixture can occur for about one hour to decolor the supernatant liquid and L-Citrulline. In step 136, the activated carbon can be removed. For example, the activated carbon can be removed by filtration, such as with a frame filter. The supernatant liquid can then be concentrated in step 138. The liquid can be concentrated under vacuum at about 70-80° C. or other suitable or desired temperature with a concentration rate of about 3:1 or other suitable or desired ratio. In step 140, the concentrated liquid can then be mixed with an appropriate amount of an organic liquid. For example, the concentrated liquid can be placed into the crude crystallization tank and a volume of ethanol can be added that is about 3 times the volume of the concentrated liquid. The mixture of concentrated liquid and ethanol can then be cooled to crystallize the L-Citrulline in step 142. The resulting material can be cooled to about 5-8° C. and blended for about 1 hour as a representative, non-limiting condition to accomplish crystallization. In step 144, the crystallized L-Citrulline is separated. The resulting crystals can be separated with bag centrifuge, resulting in a crude product that is obtained and sent to the next step.

The crystallized L-Citrulline can be dissolved in deionized water and activated carbon can be added in step 146. The crude crystals are dissolved in a volume of deionized water that can be, in some embodiments, about 1.0-1.5 times the volume of crystals and about 1.0% activated carbon is added. In step 148, the resulting mixture is heated and blended. For example, the mixture can be heated to between about 50° C. and about 70° C. The material is blended and decolored for about 1 hour. After a suitable interval of heating and blending, the activated carbon can be removed in step 150. For example, the activated carbon can be removed with a frame filter. The resulting liquid can then be cooled to crystallize the L-Citrulline in step 152. For example, the decolored liquid can be transferred to a suitable recrystallization tank and cooled to about 5-8° C. with blending for about 1 hour to promote crystallization, as representative conditions. In step 154, the second product crystallized L-Citrulline is separated. For example, the crystallized material can be separated by bag centrifuge and the second crude product can be obtained and sent to the next step.

4. Second Recrystallization and Drying and Package Procedure

The second product of L-Citrulline crystals is dissolved in deionized water to create a mixture in step 156. For example, the second crude product is dissolved in about 5-6 times volume of deionized water. In step 158, the mixture of dissolved second product of L-Citrulline and deionized water can be filtered, for instance, with a 5K molecular weight membrane. In step 160, the filtrate can then be concentrated.

The filtrate is concentrated under vacuum at about 80° C. with a concentration ratio of about 3:1, as representative conditions. The concentrated liquid can then be cooled to crystallize a third product of L-Citrulline in step 162. For example, the concentrated liquid is cooled to about 5-8° C. and allowed to crystallize for about 1 hour. The third product of L-Citrulline crystals can be separated in step 164. As above, the L-Citrulline crystals can be separated from the liquid by bag centrifuge. Then, in step 166, the L-Citrulline material can be processed for use. For example, the moist third product of L-Citrulline crystals obtained from separation in the bag centrifuge can be dried and packaged to obtain the final product.

EXAMPLES

The following Examples have been included to illustrate modes of the presently disclosed subject matter. In light of the present disclosure and the general level of skill in the art, those of skill will appreciate that the following Examples are intended to be exemplary only and that numerous changes, modifications, and alterations can be employed without departing from the scope of the presently disclosed subject matter.

Trial manufacturing and pilot production of Citrulline API have been performed. Two trial batches have produced in 15 L fermentors that were followed by two pilot scale batches. The trial batches and pilot productions are explained in more detail below.

The purification of the crude material process includes endotoxin reduction and crystallization steps.

Two batches of 10L each as well as a scaled-up consignment have been produced following the process of fermentation, extraction and refinement. The first batch began with 1 kg of arginine and resulted in the harvest of 9 L of liquor. The liquor was ultra-refined with 5 K membrane to remove endotoxin and yield 504 g of L-Citruline product. The net weight of L-Citrulline recovered from the stock solution is 685 g.

The second batch began with 1 kg of arginine and resulted in the harvest of 9 L of liquor. After extraction and endotoxin removal with 10 K ultra-filter, 160 g of good quality L-Citrulline product was obtained. L-Citrulline recovered from the stock solution weighs 963 g.

A minor alteration in processing conditions was introduced after the first batch. Initially, the fermentation broth was filtered and the resulting mycel was used to convert arginine, hence the color of the intermediate product from the first batch appeared paler. A second crystallization process was implemented before obtaining the final product. However, in the second batch, the fermentation broth was used to convert arginine directly. The color of broth was therefore brought into the inversion liquor. This resulted in a solution of darker appearance. At the extraction stage, the number of recrystallization operations was increased. The expected yield was not high due to the high quantity of Citrulline present in the stock solution. Reduction of the concentration of Citrulline in the stock solution should result in improved yield.

A scale-up batch was executed with 75 kg arginine. The processing of inversion liquor was extended over three episodes. The crude material yielded can be processed by endotoxin reduction, filtration, drying, and inspection before the final purified product can be collected.

The validation of trial batches and the scaled-up pilot batches were commenced in the pilot plant facilities. Validation was performed in two batches using 15 L fermentation. This was followed by the pilot scale production. Results are outlined below in Table I.

TABLE I

| Batch | Ferment Capacity | Qty of Starting Material | Extract Method | Yield | Cycle Time |
|---|---|---|---|---|---|
| 070701 | 15 L | 1 kg | Centrifuge | 92% | 52 Hr |
| 070702 | 15 L | 1 kg | Ultrafiltration | 93% | 93 Hr |
| 070703 | 2 T | 75 kg | Centrifuge | 92% | 46 Hr |
| 070704 | 2 T | 100 kg | Ultrafiltration | 91% | 120 Hr |

It can be concluded from all work completed so far that extraction ultrafiltration can lead to reduced yeast activity. Extraction by tubular centrifuge may therefore be a desirable method.

Examples of Procedures to Provide Assays and Protocols

Examples of procedures to provide assays and different validation protocols have been developed to validate the manufacturing of the Citrulline obtained as described above in various forms. For example, procedures have been developed to provide assays and different validation protocols of Citrulline in various forms. For instance, procedures for Citrulline API, Citrulline for injections of 500 mg, Citrulline granules of 5 g, and Citrulline in chewable tablet form of 500 mg have been developed.

Example I

Assays Relating to Citrulline, API

Examples of procedures to provide assays and different validation protocols have been developed relating to Citrulline in active pharmaceutical ingredients ("API"). Examples of the procedures include a method of assay of Citrulline in API and method of determination of related substances/degradation products of Citrulline. Examples of the protocols include a validation protocol for an assay method of Citrulline in API and related substances method validation protocol for Citrulline.

I. Method of Assay of Citrulline, API

The objective of this example is to describe the procedure for the assay of Citrulline in API. The following is a brief listing and summary of parameters for an assay.

A. Method

The methods of determination include the Isocrated Method, the External Standard, the Single Wavelength Detection, and Quantitation by Peak Area.

B. Equipment

The equipment used in the method includes:

High Performance Liquid Chromatography (HPLC) with variable UV/Vis detector, auto injector and suitable data processor/recorder;

an analytical balance; and an ultrasonic bath.

C. Reagents

Citrulline RS;

Ammonium sodium phosphate, AR;

Phosphoric acid, AR;

Acetonitrile, HPLC grade; and

Purified Water, graded suitable for chromatographic system

D. Chromatographic System/Conditions
1. Column: Type: YMC-Pack Diol-120-NP
   Dimensions: 4.6 mm (i.d)×25 cm
   Particle Size: 5 μm
   Temperature: 40° C.
2. Diluent: Water: Acetonitrile (1:1)
3. Wavelength: 200 nm
4. Injection volume: 10 μL
5. Mobile phase: Flow Rate: 2.0 mL/min
   Total Run Time: 12 minutes
   Mobile phase: Ammonium sodium phosphate solution (pH2.0) (Dissolve 1.15 g of Ammonium sodium phosphate with 800 ml of water. Adjust with Phosphoric acid to a pH of 2.0. Dilute with water to 1000 mL.):Acetonitrile=20:80. Mix well. Filter and degas.
   It should be noted that the ratio of the compositions should be kept constant when preparing the mobile phase.

E. Standard Solution Preparation
   Accurately weigh about 50 mg of Citrulline RS and transfer into a 100-ml volumetric flask. Dissolve and dilute to volume with diluent. Mix well to obtain a solution having a known concentration of about 500 μg/mL. Prepare in duplicate as std-1 and std-2.

F. System Suitability Test
1. Inject 10 μl of mobile phase and diluent each to check baseline noise and drift or any other sign of system stability. Repeat injections until the system is stable.
2. Inject 10 μl of std-1.
3. Compare the retention time (RT) with the typical RT. The typical RT is approximately 7.0±1.0 minutes for Citrulline.
4. Calculate the capacity factor (k'), Take appropriate action when k' is less than 2.5.
5. Calculate the column efficiency (N) using a Citrulline peak. Take appropriate action when the theoretical plates are less than 3000.
6. Calculate the tailing factor (T) using a Citrulline peak. Take appropriate action when the tailing factor (T) is greater than 2.0.
7. Consecutively inject six std-1.
8. Calculate the mean and relative standard deviation (RSD) of Citrulline peak area from six injections of std-1.
9. Take appropriate action when an RSD of more than 2.0% is found.

G. Calibration
1. Inject three std-2.
2. Calculate the mean peak area and RSD of Citrulline from 3 injections of std-2.
3. Take appropriate action if RSD is more than 2.0%.
4. Calculate the accuracy of std-2 against std-1 as follows:

$$\frac{A_{std.2} \times W_{std.1} \times 100}{A_{std.1} \times W_{std.2}} = 98.0 \sim 102.0\%$$

Where:
$A_{std.1}$=Mean peak area of Citrulline in the std-1 chromatograms
$A_{std.2}$=Mean peak area of Citrulline in the std-2 chromatograms
$W_{std.1}$=Weight of the Citrulline Reference Standard of std-1, in mg
$W_{std.2}$=Weight of the Citrulline Reference Standard of std-2, in mg It should be noted to take appropriate action when the recovery of std-2 is not between 98.0-102.0% using the formula above, H. Sample Solution
   Sample Solution for Assay (Spl.1) is prepared in duplicate. Accurately weigh about 50 mg Citrulline and transfer into a 100-mL volumetric flask. Dissolve and dilute to volume with diluent. Mix well to obtain a solution having a known concentration of about 500 μg/mL of Citrulline.

I. Quantitation
1. Use the results of six consecutive injections of std-1 for quantitation. If calibration is performed just prior to sample injections, these results may be used.
2. Inject two 10 μL of assay sample solution (Spl.1).
3. Inject 10 μL of std-1 every 6-12 injections to check the retention time and the peak area of Citrulline. If a deviation of more than 2.0% is found when compared with the average of 6 system suitability injections, conduct the system suitability test again to ensure there is no carry-over from previous injections and the system is stable.

J. Calculation
   Calculation of the potency for each injection using the mean peak area of std-1 as follows:

$$\text{Assay \%} = \frac{A_{Spl.1} \times W_{Std.1} \times P \times 100}{A_{Std.1} \times W_{Spl.1}}$$

Where:
$A_{Std.1}$=Mean peak area of Citrulline in the Std chromatograms
$A_{Spl.1}$=Peak area of Citrulline in the sample solution chromatogram
$W_{Std.1}$=Weight of Citrulline RS in RSD, in mg
$W_{Spl.1}$=Weight of Citrulline in the sample
P=Purity of Citrulline RS II. Validation Protocol for the Assay of Citrulline, API
The objective of this example is to describe the procedure to validate and demonstrate the suitability of the assay method for the production of Citrulline API as described above.

This example outlines a detailed validation plan for the HPLC assay test method for Citrulline as a raw material. The example validates the assay method employing High Performance Liquid Chromatography (HPLC) with Ultraviolet (UV) detection for the quantifying of Citrulline. The suitable wavelength for the detection of Citrulline is the maximum of about 200 nm. The validation of the method is accomplished by following USP/NF current guidelines for API. The protocol describes in detail the proposed experiments and acceptance criteria for the validation of the method for the determination of Citrulline in a raw material form. The following analytical test characteristics are evaluated: specificity (sample matrix interference, known impurities interference, stability-indicating studies, and forced degradation), linearity, range, precision (injection repeatability), precision (analysis repeatability), intermediate precision (ruggedness), accuracy, robustness, a filter study and the stability of solutions.

The known related compounds are Arginine and Ornithine. All of these compounds are both process impurities and degradation products. All the tests listed above are conducted following the assay analytical method outlined above. USP-current, EP (Fifth Edit and supplements), ICH guidelines are used as references.

A. Method Set Up

1. Chromatographic System and Parameters

| Pump: | Agilent 1200 |
|---|---|
| Detector: | Agilent 1200 |
| Auto sampler: | Agilent 1200 |
| Column Oven: | Agilent 1200 |
| Column: | YMC-Pack Diol-120-NP Dimensions: 250 mm × 4.6 mm (ID), particle size 5.0 µm |
| Column Temperature: | 40° C. |
| Mobile Phase: | Buffer: Acetonitrile (1:4) |
| Flow Rate: | 2.0 mL/minute |
| Injection Volume: | 10 µl |
| Detector & Wavelength: | UV at 200 nm |
| Run Time: | 12 minutes or as appropriate |

2. Materials

CITRULLINE RS
CITRULLINE, API
Arginine
Ornithine

3. Reagents

| Acetonitrile | HPLC Grade |
|---|---|
| Water | De-ionized |
| Ammonium sodium phosphate | A.R. Reagent |
| Phosphoric acid | A.R. Reagent |
| Hydrochloric Acid (HCl), (36.5-38.0%) | A.R. Reagent |
| Sodium Hydroxide (NaOH) | A.R. Reagent |
| Hydrogen Peroxide, 30% ($H_2O_2$) | A.R. Reagent |

4. Preparation of the Ammonium Sodium Phosphate Solution (pH 2.0)

Dissolve 1.15 g of Ammonium sodium phosphate in 800 mL of water. Adjust with Phosphoric acid to a pH of 2.0. Dilute with water to 1,000 mL and mix well.

5. Preparation of the Mobile Phase

In a suitable flask, prepare a 1:4 mixture of Ammonium sodium phosphate solution (pH 2.0) and Acetonitrile (v/v) and then filter through a 0.45 µm Econofilter and degas prior to use. The mixture should not be degassed for an extended period of time since evaporation of the organic solvent may alter the characteristics of the chromatographic system.

6. Preparation of the Diluent

In a suitable flask, prepare a 1:1 mixture of water and Acetonitrile (v/v).

7. Preparation of Standard Solutions

Weigh accurately about 50 mg of Citrulline RS, transfer into a 100-mL volumetric flask. Add about 80 mL of diluent and sonicate with occasional shaking for 10 minutes. Allow the solution to equilibrate to room temperature and then dilute to volume with diluent and mix well to obtain a standard solution having a known concentration of about 500 µg/mL. Prepare in duplicate as std-1 and std-2.

8. API Assay Working Sample Preparation

Accurately weigh and quantitatively transfer about 50.0 mg of Citrulline raw material into a 100-mL volumetric flask. Add about 80 mL of diluent and sonicate with occasional shaking for 10 minutes. Allow the solution to equilibrate to room temperature and then dilute to volume with diluent and mix well (Concentration: about 500 µg/mL Citrulline).

B. System Suitability

The system suitability test is conducted as required by the test method. The column is equilibrated for about an hour prior to injection of the system suitability solution. The standard solution is used for the system suitability. After the chromatographic system is equilibrated, one injection of the resolution solution and six injections of the standard solution is performed. The precision (RSD), tailing factor (T), Capacity factor (k') and theoretical plates (N) is calculated. Acceptance criteria include: system precision (RSD) being not more than ("NMT") 2.0%; the Capacity factor (k') calculated from the Citrulline peak being not less than ("NLT") 2.5; tailing Factor (T) being NMT 20 (Citrulline); and the plates (N) being NLT 3000 (Citrulline).

C. Specificity

For all tests listed in the specificity study for recording UV spectra and peak purity determination use a DAD detector.

1. Dilute Interference

Inject 10 µl of the diluent.

2. Arginine and Ornithine Solutions

Separately weigh and transfer about 25 mg each of Arginine and Ornithine into two 50-mL volumetric flasks. Add about 40 mL of diluent and sonicate with occasional shaking for 10 minutes. Allow the solution to equilibrate to room temperature and then dilute to volume with diluent and mix well.

3. Standard Spiked Sample Solution

Weigh and transfer about 25 mg each of Citrulline RS, Arginine and Ornithine into one 50-mL volumetric flask. Add about 40 mL of diluent and sonicate with occasional shaking for 10 minutes. Dilute to volume with diluent and mix well.

4. Injection Sequence

Injection Sequence includes:

| Mobile phase | 2 injections | 30 minutes |
|---|---|---|
| Diluent | 2 injections | 30 minutes |
| Standard solution 1 | 6 injections | 12 minutes |
| Standard solution 2 | 3 injections | 12 minutes |
| Arginine solution | 2 injections | 30 minutes |
| Ornithine solution | 2 injections | 30 minutes |
| Standard spiked sample solution | 2 injections | 30 minutes |

The chromatograms should be plotted at attenuation corresponding to full scale of the respective active peak. In addition, the chromatograms should be re-plotted with more sensitive attenuation to allow better examination for possible interference.

The validity criteria can comprise meeting the system suitability requirements. For acceptance criteria, examination of the diluent, Arginine solution, Ornithine solution and standard spiked sample solution chromatograms should not indicate any significant interference from peaks occurring at the retention time of the active peak at the analytical wavelength. Any peak found in the retention time window of Citrulline is NMT 0.5%. The peak purity of Citrulline, Arginine and Ornithine should be not less than 990.

5. Stability Indicating Study of Citrulline

The stability indicating studies for the Citrulline will be conducted in accordance with the following conditions listed. If extensive degradation is observed, then the particular stress condition causing the extensive degradation may be repeated using milder conditions.

i. Preparation of Sample for Test

Accurately weigh and quantitatively transfer about 50.0 mg of Citrulline raw material into a 100-mL volumetric flask. Prepare three additional volumetric flasks with raw material powder.

ii. Ambient Control

Let one of the volumetric flasks prepared according to section (C)(5)(i) above stand (capped) on the bench for 72 hours. After 72 hours, add about 80 mL of diluent and sonicate with occasional shaking for 10 minutes. Allow the solution to equilibrate to room temperature and then dilute to volume with diluent and mix well. Filter about a 10-mL portion of the sample through a 0.45 μm Agilent Regenerated Cellulose Filter into a suitable container after discarding the first 3 mL.

iii. Light

Quantitatively transfer about 500 mg of Citrulline raw material into an open container. Spread the powder out in as thin a layer as possible and then place under a light (700 Watt/m$^2$) for 28 hours. Quantitatively transfer about 50 mg of Citrulline raw material powder into a 100-mL volumetric flask. Add about 80 mL of diluent and sonicate with occasional shaking for 10 minutes. Allow the solution to equilibrate to room temperature and then dilute to volume with diluent and mix well. Filter about a 10-mL portion of the sample through a 0.45 μm Agilent Regenerated Cellulose Filter into a suitable container after discarding the first 3 mL.

iv. Heat

Quantitatively transfer about 500 mg of Citrulline raw material into an open container. Spread the powder out in as thin a layer as possible and place it in an oven at 105° C. and let stand for 24 hours. Take out the container from oven. Allow to cool. Accurately weigh and quantitatively transfer about 50.0 mg of Citrulline raw material into a 100-mL volumetric flask. Add about 80 mL of diluent and sonicate with occasional shaking for 10 minutes. Allow the solution to equilibrate to room temperature and then dilute to volume with diluent and mix well. Filter about a 10-mL portion of the sample through a 0.45 μm Agilent Regenerated Cellulose Filter into a suitable container after discarding the first 3 mL.

v. Acid Hydrolysis

To one of the volumetric flasks prepared according to section (C)(5)(i) above, add about 20 mL of 1N HCl and place at room temperature for about 72 hours with occasional shaking. After 72 hours, add about 20 mL of 1N NaOH to neutralize to a pH of 7 and then add about 40 mL of diluent. Sonicate with occasional shaking for 10 minutes. Allow the solution to equilibrate to room temperature and then dilute to volume with diluent and mix well. Filter about a 10-mL portion of the sample through a 0.45 μm Agilent Regenerated Cellulose Filter into a suitable container after discarding the first 3 mL.

vi. Base Hydrolysis

To one of the volumetric flasks prepared according to section (C)(5)(i) above, add about 20 mL of 1N NaOH and place at room temperature for about 72 hours with occasional shaking. After 72 hours, add about 20 mL of 1N HCl to neutralize to a pH of 7 and then add about 40 mL of diluent. Sonicate with occasional shaking for 10 minutes. Allow the solution to equilibrate to room temperature and then dilute to volume with diluent and mix well. Filter about a 10-mL portion of the sample through a 0.45 μm Agilent Regenerated Cellulose Filter into a suitable container after discarding the first 3 mL.

vii. Oxidation

To one of the volumetric flasks prepared according to section (C)(5)(i) above, add about 20 mL of 5% $H_2O_2$ and place at room temperature for about 72 hours with occasional shaking. After 72 hours, add about 50 mL of diluent, sonicate with occasional shaking for 10 minutes. Allow the solution to equilibrate to room temperature and then dilute to volume with diluent and mix well. Filter about a 10-mL portion of the sample through a 0.45 μm Agilent Regenerated Cellulose Filter into a suitable container after discarding the first 3 mL.

viii. Chromatographic Procedure

Run a system suitability and calibration as described herein. A procedure control standard is placed between every two hours and at the end of the sequence. Peak purity analysis will be performed for all the samples to assess the peak purity of the Citrulline and to ensure the absence of any significant interference from degradation peak. Calculate the percent of Citrulline found in the stressed samples versus the standard solution as determined in the system suitability.

The validity criteria can comprise meeting the system suitability requirements. For acceptance criteria, under all stress conditions the appreciable degradation peaks are resolved from the active peak. The peak purity analysis should indicate the absence of any significant chromatographic interference from the degradation compounds for the Citrulline peak. Any peak found in the retention time window of Citrulline is NMT 0.5%. The peak purity of Citrulline should be not less than 990.

System suitability results should report the percentage of any peak, found in the retention time window of Citrulline from the analysis of the diluent blank. The mass of raw material, the exposure conditions and time, the percent Citrulline found, the purity data and the resolution for the closest peak to the Citrulline peak should be tabulated.

D. Standard Linearity

The working concentration of the standard solution is about 500.0 μg/mL Citrulline. The linearity and range study is carried out over a concentration range of 100.0 μg/mL to 1,000.0 μg/mL. This represents a range of 20% of the working standard concentration to 200% of the working standard concentration.

1. Preparation of Linearity Stock Solution

Weigh accurately about 500 mg of Citrulline RS and transfer into a 100-mL volumetric flask. Add about 80 mL of diluent and sonicate with occasional shaking for 10 minutes. Allow the solution to equilibrate to room temperature and then dilute to volume with diluent and mix well to obtain a solution having a known concentration of about 5.0 mg/mL. This is the Linearity Stock Solution.

2. Preparation of Linearity Solutions

Use the "Linearity Stock Solution" to prepare the linearity solutions as shown in the following table using volumetric pipettes and volumetric flasks. Dilute to volume with Diluent and mix well.

| Level # | % Working Standard | Dilution Scheme mL of Stock Standard | Final Volume (mL) | Approx. Concentration of Citrulline (μg/mL) |
|---|---|---|---|---|
| 1 | 20 | 2.0 | 100.0 | 100.0 |
| 2 | 40 | 4.0 | 100.0 | 200.0 |
| 3 | 60 | 6.0 | 100.0 | 300.0 |
| 4 | 80 | 8.0 | 100.0 | 400.0 |
| 5 | 100 | 10.0 | 100.0 | 500.0 |
| 6 | 140 | 14.0 | 100.0 | 700.0 |
| 7 | 160 | 16.0 | 100.0 | 800.0 |
| 8 | 200 | 20.0 | 100.0 | 1000.0 |

3. Procedure

Run system suitability as described herein using a freshly prepared working standard. For each of the eight linearity solutions, inject the solutions in triplicate as described in herein. Plot the analyte concentration on the abscissa and corresponding average area on the ordinate axis. Perform a linear regression on the data. The y-intercept should be near zero (0), calculate the ratio of the fitted y-intercept value over the average response at 100% level (y-bias). Calculate, for each level, the percent relative standard deviation (% RSD), the response factor (RF) and the relative response factor (RRF—relative to the response factor of the 100% level, 500.0 μg/mL).

The validity criteria can comprise meeting the system suitability requirements. The % difference between duplicate injections is NMT 2.0%. For acceptance criteria, the correlation coefficient is NLT 0.999. The mean relative response factors for each concentration level are between 97.0% to 103.0% relative to the L5 level. The y-intercept is NMT 2% of area in 100% level.

E. Accuracy

1. Preparation of the 50% Accuracy Samples

Accurately weigh and quantitatively transfer about 25 mg of Citrulline RS into a 100-mL volumetric flask. Add about 80 mL of diluent and sonicate with occasional shaking for 10 minutes. Allow the solution to equilibrate to room temperature and then dilute to volume with diluent and mix well. Prepare 2 additional samples (Concentration: about 250 μg/mL Citrulline).

2. Preparation of the 100% Accuracy Samples

Accurately weigh and quantitatively transfer about 50 mg of Citrulline RS into a 100-mL volumetric flask. Add about 80 mL diluent and sonicate with occasional shaking for 10 minutes. Allow the solution to equilibrate to room temperature and then dilute to volume with diluent and mix well. Prepare 2 additional samples (Concentration: about 500 μg/mL Citrulline).

3. Preparation of the 150% Accuracy Samples

Accurately weigh and quantitatively transfer about 75 mg of Citrulline RS into a 100-mL volumetric flask. Add about 80 mL diluent and sonicate with occasional shaking for 10 minutes. Allow the solution to equilibrate to room temperature and then dilute to volume with diluent and mix well. Prepare 2 additional samples (Concentration: about 750 μg/mL Citrulline).

Validity Criteria:

Meets system suitability requirements.

Inject each recovery solution in duplicate. The difference between duplicate injections is NMT 2.0%.

Acceptance Criteria:

Mean Recovery from the matrix between each concentration level is between 98.0% and 102.0%.

Precision (RSD) for the recoveries of the triplicate sample preparations within the same concentration level is NMT 2.0%.

F. Precision

1. Repeatability

Six working sample solutions are prepared as described herein. The precision of the method will be determined by performing six assays of Citrulline at 100% of the working sample concentration in three consecutive days. Run system suitability and calibration as described herein. Each of the sample solutions will be then injected in duplicate and a procedural control standard should be placed between every two hours and at the end of the sequence, Validity Criteria:

Meets the system suitability requirements.

The % difference between duplicate injections is NMT 2.0%,

Acceptance Criteria:

The RSD of the six preparations for each day should be NMT 20%.

The overall RSD of mean assay for three days should be NMT 2.0%.

2. Intermediate Precision

The intermediate precision of the Citrulline assay analysis procedure is evaluated by performing six assays from the same lot of the Citrulline API used in section (F)(1) above, entitled "Repeatability," following the sample solution preparation and test procedures described in this protocol. The intermediate precision should be conducted independently by another analyst, using a different HPLC system, a different column and on a different day.

Run system suitability and calibration as described herein. Each of the sample solutions will be injected in duplicate and a procedural control standard should be placed between every two hours and at the end of the sequence.

Validity Criteria:

Meets the system suitability requirements.

The difference between duplicate injections is NMT 2.0%.

Acceptance Criteria:

The RSD of replicate preparations should be NMT 2.0%.

Difference of the means of the analysts should be NMT 2.0%.

G. Standard and Sample Solution Stability

1. Preparation of Standard Solution

Weigh accurately about 50 mg of Citrulline RS and transfer into a 100-mL volumetric flask. Add about 80 mL of diluent and sonicate with occasional shaking for 10 minutes. Allow the solution to equilibrate to room temperature and then dilute to volume with diluent and mix well to obtain a standard solution having a known concentration of about 0.5 mg/mL. Prepare in duplicate as std-1 and std-2.

2. Preparation of Standard Stability Solution

Weigh accurately about 50 mg of Citrulline RS, transfer into a 100-mL volumetric flask. Add about 80 mL of diluent and sonicate with occasional shaking for 10 minutes. Allow the solution to equilibrate to room temperature and then dilute to volume with diluent and mix well to obtain a solution having a known concentration of about 0.5 mg/mL.

3. Preparation of Sample Stability Solution

Accurately weigh and quantitatively transfer about 50.0 mg of Citrulline raw material into a 100-mL volumetric flask. Add about 80 mL of diluent and sonicate with occasional shaking for 10 minutes. Allow the solution to equilibrate to room temperature and then dilute to volume with diluent and mix well (Concentration: about 500 μg/mL Citrulline).

4. Procedure

Run system suitability and calibration test. Inject the standard and sample solution every hour over the course of 48 hours.

Validity Criteria:

Meets the system suitability requirements.

Acceptance Criteria:

The standard and the sample solutions will be considered stable if the results at each time point are within ±2% of the initial results.

H. Robustness Study

It is a measure of the method's capability to remain unaffected by small, but deliberate variations in method parameters. The following parameters are independently varied in this study: mobile phase flow rate, column temperature, buffer pH and organic phase composition of the mobile phase.

1. Preparation of the Standard Solution

Prepare a working standard as described in ARD-DSTM031A.

2. Preparation of the API Assay Sample Solution

Prepare a API Assay Working Sample as described in ARD-DSTM031A. A previously prepared sample solution can be used.

3. Mobile Phase Flow Rate Variations

The flow rate is varied by ±0.2 mL/minute. The method flow rate of 2.0 mL/minute and the varied flow rates of 2.2 mL/minute and 1.8 mL/minute are evaluated.

4. Column Temperature Variations

The column temperature is varied by ±5° C. The method column temperature of 40° C. and the varied column temperatures of 35° C. and 45° C. are evaluated.

5. Buffer pH Variations

The buffer pH composition is adjusted to 1.8 and 2.2 respectively. Prepare the buffer as specified herein and measure the pH. Divide this preparation into three portions. Use a 0.5 N sodium hydroxide solution to raise the pH up about 0.2 units. Use a 0.5 N phosphoric acid solution to lower the pH down about 0.2 units. Prepare three Mobile Phases with these Buffers.

6. Organic Phase Composition Variations

The organic phase composition will be varied by about ±2%. Prepare mobile phases at the method specified ratio of 20% Buffer: 80% Acetonitrile and at the varied ratios of 18% Buffer: 82% Acetonitrile and 22% Buffer: 78% Acetonitrile.

7. Procedure

Run system suitability standards as described in ARD-DSTM031A followed by 2 injections of the Working Assay Sample Solution. Calculate the Percent Found of Citrulline for each condition using the average area from the six system suitability standards for that condition Validity Criteria:

Meets the system suitability requirements for each I-IPLC condition.

Acceptance Criteria:

The percent Citrulline found in the Citrulline Granules Assay sample is between 95.0% and 105.0% for the method specified parameters.

The RSD is NMT 3.0% between the value calculated when the parameters are changed and not changed.

I. Filtration Study

The filtration step used in the sample preparation is validated to assure that the filter element does not interfere with the quantitation of the active. The filter used for the filtration of the sample is a 0.45 μm regenerated cellulose membrane filter (Agilent). The working standard solution and a sample solution are prepared as described herein.

1. Preparation of Standard Solution

Prepare a standard solution as specified herein. Prepare in duplicate as std-1 and std-2.

2. Preparation of Filtered Standard Solution

Use the std-1 prepared according to section (I)(1) above. Filter the standard solution through a 0.45 μm Agilent Regenerated Cellulose Filter, discarding the initial 1 mL to saturate the filter. Then filter another 1 mL into an autosampler vial for analysis, repeat this step nine more times to obtain ten samples in total for injection. Fill one vial with unfiltered standard solution. Use the std-2 to prepare another eleven samples with the same method.

3. Preparation of Filtered Blanks

Filter the diluent through a 0.45 μm Agilent Regenerated Cellulose Filter, discarding initial 3 mL to saturate the filter, and fill an autosampler vial for analysis.

4. Procedure

Run a system suitability test as described herein using a freshly prepared working standard. Make one injection of the filtered diluent, the filtered standard fractions, and the unfiltered standards as described herein. Calculate, as area percentage of the average area from system suitability working standard injections, any peaks found in the retention time window of Citrulline from the Filtered Diluent Blank injections. Calculate the percent recovery for the filtered standards and the unfiltered standards.

Validity Criteria

Pass System Suitability Requirement. Any peak found in the retention time window of Citrulline from the filtered medium blanks is less than 0.5% of the average area of the working standard. The mean recovery from the filtered standards is within ±2.0% of the mean recovery from the unfiltered standards.

Acceptance Criteria

The mean recovery from the filtered standards is within ±2.0% of the mean recovery from the unfiltered standards.

J. Extraction Study

The extraction step used in the sample preparation will be validated to assure that the quantitation of the active won't be interfered.

1. Preparation of Standard Solution

Weigh accurately about 50 mg of Citrulline RS, transfer into a 100-mL volumetric flask. Add about 80 mL of diluent and sonicate with occasional shaking for 10 minutes. Allow the solution to equilibrate to room temperature and then dilute to volume with diluent and mix well to obtain a standard solution having a known concentration of about 0.5 mg/mL. Prepare in duplicate as std-1 and std-2.

2. Preparation of Sample Solution

Weigh accurately six portions of 50 mg Citrulline raw material and transfer into six 100-mL volumetric flasks, respectively. Add about 80 mL of diluent, extract according to the procedure described in the table below. Then, allow the solution to equilibrate to room temperature. Dilute to volume with diluent and mix well.

| Spl. No. | Mix as |
|---|---|
| 1 | Sonicate with occasional shaking for 5 minutes |
| 2 | Sonicate with occasional shaking for 5 minutes |
| 3 | Sonicate with occasional shaking for 10 minutes |
| 4 | Sonicate with occasional shaking for 10 minutes |
| 5 | Sonicate with occasional shaking for 15 minutes |
| 6 | Sonicate with occasional shaking for 15 minutes |

3. Procedure

System suitability and calibration are established as described in herein. Each of the sample solutions is injected in duplicate. A procedural control standard should be injected after every six injections of sample and at the end of the sequence.

The recoveries of the solution are calculated versus the standard solution as determined in the system suitability. The resulting data is evaluated to determine the extraction procedure. The extraction time indicated by the method should be longer than that mandated by the validation.

Validity Criteria

Meet system suitability requirements.

The data is evaluated for trends due to the extraction. In general, if no trend is observed in the various samples, sonicate with occasional shaking for 5 minutes to extract Citrulline. If a clear trend is observed, extraction for adequate time is conducted to assure there is no interference.

Acceptance Criteria

The mean recovery of the sample sonicated for administered extracting time is within ±2.0% from the recovery of the sample sonicated for the time of the time point next to it.

K. Range

The range of the assay test method is determined by the linearity and accuracy.

L. Conclusions

The method is considered validated if specificity, accuracy, linearity, precision, robustness, filtration, extraction, and range results meet predefined validity & acceptance criteria.

III. Method of Determination of Related Substances/Degradation Products of Citrulline The objective of this example is to define the procedure to determine related substances/degradation products in Citrulline. The following is a brief listing and summary of parameters of the method.

A. Method

The methods of determination include the Gradient Method, the External Standard, the FLD Detection, and the Quantitation by Peak Area.

B. Equipment

The equipment used in the method includes:
HPLC with variable Fluorometry detector, auto injector, and suitable data processor/recorder;
one pump for reagent transport;
a reaction coil with thermostat: A column 0.25 μm (inside diameter) and 5 m in length;
an analytical balance;
an ultrasonic bath; and
a Regenerated Cellulose Membrane Filter-Agilent.

C. Test Articles

Citrulline RS (SIGMA);
Ornithine RS (SIGMA);
Arginine RS (USP);
Anhydrous sodium sulfate, AR;
Sodium I-heptane sulfonate, HPLC grade;
Acetic acid, AR;
Boric acid, AR;
2-mercaptoethanol, AR;
Potassium chloride, AR;
Sodium hydroxide, AR;
O-phthalaldehyde, AR;
Ethanol, AR;
Methanol, HPLC grade; and
Purified Water, graded suitable for chromatographic system D. Chromatographic System/Conditions 1. Column: Type: AQ C18
   Dimensions: 4.6 mm (i.d.)×25 cm
   Particle Size: 5.0 μm
   Temperature: 20° C.
2. Diluent: water
3. Detector: Fluorometry (excitation wavelength: 340 nm, detection wavelength: 450 nm), GAIN: 8.
4. Mobile phase: Flow Rate: 0.8 mL/min
   Total Run Time: 60 min
   Solution A: Dissolve 28.4 g of anhydrous sodium sulfate and 5.2 g sodium I-heptane sulfonate in 1,000 mL of water. Add 1 mL of acetic acid, and mix well, Filter and degas.
   Solution B: Methanol
   Mobile phase A: Solution A.
   Mobile phase B: Filter and degas a mixture of Solution A and Solution B at 80:20 ratio.

The chromatograph is programmed as follows:

| Time (minutes) | Solution A (%) | Solution B (%) | Flow rate (mL/min) |
|---|---|---|---|
| 0 | 100 | 0 | 0.8 |
| 6 | 100 | 0 | 0.8 |
| 8 | 0 | 100 | 0.8 |
| 40 | 0 | 100 | 0.8 |
| 41 | 100 | 0 | 0.8 |
| 60 | 100 | 0 | 0.8 |

It should be noted that the ratio of the mobile phase solution should be kept constant when preparing the mobile phase.

5. Reagent: Dissolve 6.2 g boric acid, 7.4 g potassium chloride, 3.5 g sodium hydroxide in 1000 mL of water, add 10 mL of a solution of o-phthalaldehyde in ethanol (4 g in 25 mL ethanol) and 4 mL of 2-mercaptoethanol.
6. Reaction temperature: the reaction temperature can be maintained at a constant temperature of 30° C.
7. Flow rate of the reagent: the flow rate of the reagent can be 0.5 mL per minute.

E. Standard Solution Preparation

Weigh accurately about 100.0 mg of Citrulline RS and transfer into a 100-mL volumetric flask. Dissolve and dilute to volume with diluent to obtain a solution having a known concentration of about 1,000 μg/mL. Pipette 1.0 mL of the solution into a 200-mL volumetric flask. Dilute to volume with diluent and mix well. The concentration of Citrulline is about 5.0 μg/mL. The resulting solution will be referred to as std. in this section.

F. Resolution Solution Preparation (RS)

Weigh accurately about 10.0 mg of Citrulline RS and 10.0 mg Ornithine RS into a 100-mL volumetric flask. Dissolve and dilute to volume with diluent. Mix well to obtain a solution having a known concentration of about 100 μg/m L. This solution is the system suitability solution.

G. System Suitability Test

1. Inject 10 μL of mobile phase and 10 μL of diluent. Check baseline noise and drift or any other sign of system stability. Repeat injections until the system is stable. Note retention time of any solvent related peaks.
2. Inject 10 μL of system suitability solution.
3. Compare the retention time (RT) with the typical RT. The typical RT is as follows:

|  | Approx. RT (min) |
|---|---|
| Citrulline | 5.0 ± 1.0 min |
| Ornithine | 7.0 ± 1.0 min |

Take appropriate action if a significant deviation from typical RT is noted.

4. Calculate the following resolution factor (R). Take appropriate action if R (between Ornithine and Citrulline) is less than 5.0.
5. Calculate the column efficiency (N) using Citrulline peak. Take appropriate action if the number of theoretical plates is less than 3,000.
6. Consecutively inject six 10 μL of std.
7. Calculate the mean and relative standard deviation (RSD) of Citrulline peak area from six injections of std.

8. Take appropriate action if an RSD of more than 5.0% is found.

H. Sample Solution (spl.)

Accurately weigh about 100 mg of Citrulline into a 100-mL volumetric flask. Dissolve and dilute to volume with water to obtain a Citrulline solution having a concentration of 1,000 µg/mL.

I. Quantitation
1. For quantitation, use the results of six consecutive injections of std. If calibration is performed just prior to sample injections, these results may be used.
2. Inject 10 µL of the sample solution (spl.) in duplicate.
3. Inject 10 µL of the standard solution (std.) every 6-12 injections to check the retention time and the peak area of Citrulline. If a deviation of more than 5.0% is found when compared with the average of six system suitability injections, conduct the system suitability test again to ensure there is no carry-over from previous injections and the system is stable.

J. Calculation
1. Quantitate known related substances using the 0.5% Citrulline standard and the appropriate response factor. The list below indicates these compounds, their retention times (RT), their relative retention (RRT) based on an RT of 5.0 minutes for Citrulline, and their relative response factors (F).

| Compound | Approx. RT (min) | RRT | F |
|---|---|---|---|
| Citrulline | 5.0 | / | / |
| Ornithine | 7.2 | 1.4 | 2.7 |
| Arginine | 18.0 | 3.6 | 1.0 |

$$\text{Related Substance} = \frac{A_{Spl} \times F \times W_{Std}/100 \text{ mL} \times 1.0 \text{ mL}/200 \text{ mL} \times P}{A_{Std} \times W_{Spl}} \times 100$$

Where:

$A_{Std}$=Mean of peak area of Citrulline in the Std chromatograms.

$A_{Spl}$=Peak area of the related compound in the sample solution chromatogram.

$W_{Std}$=Weight of the Citrulline Reference Standard of Std, in mg.

$W_{Spl.1}$=Weight of Citrulline in the sample, in mg.

F=Relative Response factor.

P=Purity of the Citrulline Reference Standard.

2. Calculate the total related substances and degradation products presenting, in percent using the following expression:

Ornithine %+Arginine %+Unknown–$Imp.a$%+$Imp.b$%+$Imp.c$%+Unknown $N$%=Total impurities %

IV. Related Substances Method Validation Protocol for Citrulline

The objective of this example is to describe the procedure to validate and demonstrate the suitability of test procedures described in the test method of determination of related substances and degradation products of Citrulline.

This example validates a stability indicating assay method for the quantitation of related compounds employing a post column derived method with High Performance Liquid Chromatography (HPLC) with FLD detection. The suitable excitation wavelength for the detection of Citrulline and its related compounds is 340 nm and the detection wavelength is 450 nm. PMT-Gain is 8. The validation of the method is accomplished by following USP/NF current guidelines. The protocol describes in detail the proposed experiments and acceptance criteria for the validation of the method.

This test method is used to determine two known related substances as well as individual and total unspecified related substances.

The following studies are conducted to ensure the method is suitable for testing Citrulline: system suitability, specificity (known impurities interference and stability-indicating studies), standard linearity, accuracy, range, precision (repeatability), intermediate precision (ruggedness), limit of detection (LOD)/limit of quantitation (LOQ), standard and sample solutions stability and robustness.

All the tests listed above are conducted following the impurities analytical method described herein. USP-current, EP (Fifth Edition and supplements), ICH guidelines are used as references.

A. Test Article
1. Article
   Citrulline RS (SIGMA)
   Ornithine RS (SIGMA)
   Arginine RS (USP)
   Anhydrous sodium sulfate, A.R
   Sodium I-heptane sulfonate, HPLC grade
   Acetic acid, AR
   Boric acid, AR
   2-mercaptoethallol, AR
   Potassium chloride, AR
   Sodium hydroxide, AR
   O-phthalaldehyde, AR
   Ethanol, A
   Methanol, HPLC grade
   Purified Water, graded suitable for chromatographic system
2. Mobile Phase Preparation
   Solution A: dissolve 28.4 g of anhydrous sodium sulfate and 5.2 g of sodium I-heptane sulfonate in 1,000 mL of water, add 1 mL of acetic acid, and mix well. Filter and degas.
   Solution B: Methanol
   Mobile phase A: Solution A.
   Mobile phase B: Filter and degas a mixture of Solution A and Solution B at 80:20 ratio.
   The chromatograph is programmed as follows:

| Time (minutes) | Solution A (%) | Solution B (%) | Flow rate (mL/min) |
|---|---|---|---|
| 0 | 100 | 0 | 0.8 |
| 6 | 100 | 0 | 0.8 |
| 8 | 0 | 100 | 0.8 |
| 40 | 0 | 100 | 0.8 |
| 41 | 100 | 0 | 0.8 |
| 60 | 100 | 0 | 0.8 |

Note: the ratio of the mobile phase solution is kept constant when preparing the mobile phase.

3. Reagent Preparation
   Dissolve 6.2 g boric acid, 7.4 g potassium chloride, and 3.5 g sodium hydroxide in 1000 mL of water. Add 10 mL of a solution of o-phthalaldehyde in ethanol (4 g in 25 mL ethanol) and 4 mL of 2-mercaptoethanol.

4. Reaction Temperature

The reaction temperature can be a constant temperature of 30° C.

5. Flow Rate of the Reagent

A flow rate of reagent can be 0.5 mL per minute.

6. Resolution Solution Preparation (RS)

Weigh out accurately about 10.0 mg of Citrulline RS and 10.0 mg Ornithine RS into a 100-mL volumetric flask. Dissolve and dilute to volume with diluent. Mix well to obtain a solution having a known concentration of about 100 µg/mL. This solution is a system suitability solution.

7. Standard Solution Preparation

Weigh out accurately about 100.0 mg of Citrulline RS and transfer into a 100-mL volumetric flask. Dissolve and dilute to volume with diluent to obtain a solution having a known concentration of about 1,000 µg/mL. Pipette 1.0 mL of the solution into a 200-mL volumetric flask. Dilute to volume with diluent and mix well. The concentration of Citrulline is about 5.0 µg/mL.

8. Sample Solution Preparation

Accurately weigh about 100 mg of Citrulline into 100-mL volumetric flask. Add water to dissolve and dilute to volume to obtain Citrulline solution at concentration of 1,000 µg/mL.

B. Experimental Parameters

HPLC Equipment System and Parameters:

| Pump: | Agilent 1200 |
| --- | --- |
| Detector: | Agilent 1100 FLD (Excitation wavelength: 340 nm, Detection wavelength: 450 nm) |
| Auto sampler: | Agilent 1200 |
| Column Oven: | Agilent 1200 |
| Column: | Type: Ultimate AQ-C18 4.6 mm (i.d.) × 25 cm, 5 µm. Ser. No: 220701594, 220701595 |
| Temperature: | 20° C. |
| Injection Volume: | 10 µL |
| Flow rate: | 0.8 mL/min |
| Run Time: | Gradient: 60 min |
| Pump for reagent transport: | SHIMADZULC-IOAT |
| Reaction coil: | A column 0.25 µm in inside diameter and 5 m in length |
| Thermostat: | Reaction temperature: 30° C. |
| Flow rate of the reagent: | 0.5 mL/min |

C. System Suitability

The system suitability test is conducted following the proposed test method described herein for the procedure to determine related substances/degradation products in Citrulline. The column is equilibrated for about an hour prior to injection of the system suitability solution. After the chromatographic system is equilibrated, one injection of the resolution solution and six injections of standard solution are performed. The precision (RSD), tailing factor (T), and theoretical plates (N) is calculated.

1. Acceptance Criteria

Perform a single 10 µL injection of the Resolution Solution. The Citrulline peak elutes at about 5.0 minutes and the Ornithine peak elutes at about 7.0 minutes. However, these times may vary.

The Resolution between Citrulline peak and the Ornithine peak is NLT 5.0.

Calculate the column efficiency (N) using Citrulline peak. The number of theoretical plates is not less than 3000.

The system precision is acceptable if the relative standard deviation (RSD) from six (6) replicate injections is not more than 5.0%.

D. Specificity

1. Known Impurity Interference i. Arginine Standard Solution

Accurately weigh 10 mg of Arginine RS into 100-mL volumetric flask. Add water to dissolve and dilute to volume to obtain Arginine RS standard solution at a concentration of 100 µg/mL.

ii. Ornithine Standard Solution

Accurately weigh 10 mg of Ornithine RS into 100-mL volumetric flask. Add water to dissolve and dilute to volume to obtain Ornithine RS standard solution at a concentration of 100 µg/mL.

iii. Standard solution

Accurately weigh 100 mg of Citrulline RS into 100-mL volumetric flask. Add water to dissolve and dilute to volume with water to obtain Citrulline RS stock solution at concentration of 1,000 µg/mL. Pipette 1 mL of the solution into a 200-mL volumetric flask. Dilute to volume with water to obtain a Citrulline RS solution at a concentration of 5 µg/mL.

iv. Spiked Control Sample Solution

Accurately weigh about 100 mg of Citrulline transfer into 100-mL volumetric flask. Accurately pipette 5.0 mL of Arginine standard solution and Ornithine stock standard solution into the 100-mL volumetric flask. Add water to dissolve and dilute to volume and mix well.

v. Uri-Spiked Control Sample Solution

Accurately weigh about 100 mg of Citrulline RS into 100 mL volumetric flask, add water to dissolve and dilute to volume with water to obtain Citrulline solution at concentration of 1000 µg/mL.

vi. Chromatographic Procedure

Run a system suitability test as described above for the procedure to determine related substances/degradation products in Citrulline. The individual impurities solution and the spiked sample solution are injected along with an unspiked control sample solution to determine the retention time to determine if the impurities can be separated from each other efficiently and any interference from these related compounds.

Injection Sequence

| Sequence | Injection Times | Running Time |
| --- | --- | --- |
| Mobile Phase A | 1 injection | 60 minutes |
| Mobile Phase B | 1 injection | 60 minutes |
| Water | 1 injection | 60 minutes |
| System suitability solution | 1 injection | 60 minutes |
| Standard solution | 6 injections | 10 minutes |
| Arginine Solution | 1 injection | 60 minutes |
| Ornithine Solution | 1 injection | 60 minutes |
| Unspiked control sample solution | 1 injection | 60 minutes |
| Spiked control sample solution | 1 injection | 60 minutes |
| Standard Solution | 1 injection | 10 minutes | vii. Acceptance Criteria

Pass system suitability requirements. Examination of water, the mobile phase A, the mobile phase B, the two known impurities, unspiked control sample solution, and impurity spiked control sample solution chromatograms should not indicate any significant interference from peaks occurring at the retention time of the active peak at the analytical wavelength. The impurities can be separated from each other efficiently. If any appreciable interference is noted, further work is required to determine the origin and extent of interference.

2. Forced Degradation

The stability indicating studies for Citrulline are conducted in accordance with the following conditions listed. If extensive degradation is observed, then the particular stress condition causing the extensive degradation may be repeated using milder conditions.

i. Un-Stressed Citrulline Control Solution

Accurately weigh about 100 mg of Citrulline RS into 100-mL volumetric flask. Add water to dissolve and dilute to volume to obtain Citrulline solution at concentration of 1,000 µg/mL.

ii. Heat Stressed Citrulline Control Solution

Expose Citrulline to an elevated temperature of 105° C. for 24 hours. Accurately weigh 100 mg of heat stressed Citrulline into 100-mL volumetric flask. Add water to dissolve and dilute to volume and mix well.

iii. Light Stressed Citrulline Control Solution

Expose Citrulline to intense white light (700 W/m2) for about 28 hours. Accurately weigh 100 mg of light stressed Citrulline into 100-mL volumetric flask. Add water to dissolve and dilute to volume and mix well.

iv. HCl Stressed Citrulline Control Solution

Accurately weigh about 100 mg Citrulline into 100-mL volumetric flask. Add 20 mL of 1.0 N HCl and mix well. Keep this solution at room temperature for 72 hours, followed by neutralization with about 20 mL of 1.0 N sodium hydroxide solution to a pH between about 5 and 7. Dilute to volume with water and mix well.

v. Alkali Hydrolysis Stressed Citrulline Control Solution

Accurately weigh about 100 mg Citrulline into 100 mL volumetric flask. Add 20 mL of 1.0 N sodium hydroxide and mix well. Keep this solution at room temperature for 72 hours, followed by neutralization with about 20 mL of 1.0 N HCl solution to a pH between about 5 and 7. Dilute to volume with water and mix well.

vi. Oxidation Stressed Citrulline Control Solution

Accurately weigh about 100 mg Citrulline into 100 mL volumetric flask. Add 20 mL of 5% Hydrogen Peroxide and mix well. Keep this solution at room temperature for 24 hours, then dilute to volume with water and mix well.

vii. Chromatographic Procedure

Run a system suitability and calibration test as described herein for the procedure to determine related substances/degradation products in Citrulline. Each above sample solutions is injected for an extended run time of 60 minutes. A procedure control standard is injected following six sample injections and at the end of the injection. Peak purity analysis is performed for all samples to assess the peak purity of Citrulline and to ensure the absence of any significant interference from degradation peak.

viii. Acceptance Criteria

Any degradant peak observed, or known impurity peak, should have a Resolution greater than 1.5 from the Citrulline peak. The Citrulline peak should be spectrally pure. Known Impurity peaks found in the five Degradation Solutions should be spectrally pure (if the signal is strong enough to assess the purity).

E. Standard Linearity

The concentration of Citrulline sample solution is 1.0 mg/mL and the working standard solution is about 5.0 µg/mL (0.5%). The linearity study is conducted for Citrulline, Arginine, and Ornithine, and the range is from LOQ to 200% of the specified limit of impurities (10.0 µg/mL).

1. Preparation of Linearity Stock Solution

Accurately weigh about 50.0 mg of each of Ornithine, Arginine and Citrulline. Quantitatively transfer into a 100-mL volumetric flask with the aid of about 50 mL of water. Sonicate to dissolve, then dilute to volume with water and mix well. Accurately pipette 10 mL of the above solution into 100-mL volumetric flask and dilute to volume with water and mix well (Concentration: each about 50 µg/mL).

2. Preparation of Linearity Solutions

Use the "Linearity Stock Solution" to prepare the linearity solutions as shown in the following table using volumetric pipettes and volumetric flasks. Dilute to volume with water and mix well.

| | | Dilution Scheme | | | |
|---|---|---|---|---|---|
| evel # | % Working Standard | mL of Linearity Solution | Final Volume (mL) | Approx. Concentration (µg/mL) | % of Test Solution |
| 1 | 10 | 1.0 | 100.0 | 0.5 | 0.05 |
| 2 | 20 | 2.0 | 100.0 | 1.0 | 0.10 |
| 3 | 40 | 4.0 | 100.0 | 2.0 | 0.20 |
| 4 | 80 | 8.0 | 100.0 | 4.0 | 0.40 |
| 5 | 100 | 10.0 | 100.0 | 5.0 | 0.50 |
| 6 | 150 | 15.0 | 100.0 | 7.5 | 0.75 |
| 7 | 200 | 20.0 | 100.0 | 10.0 | 1.00 |

3. Procedure

Run a system suitability and calibration test as described herein for the procedure to determine related substances/degradation products in Citrulline. For each of the eight linearity solutions, inject the solutions in one by one. Plot the analyte concentration on the abscissa and corresponding average area on the ordinate axis. Perform a linear regression on the data. Calculate the ratio of the fitted y-intercept value over the average response at 100% level (y-Bias). Calculate, for each level, the percent relative standard deviation (% RSD), the response factor (RF) and the relative response factor (RRF—relative to the response factor of the 100% level, 5.0 µg/mL).

4. Acceptance Criteria

Pass system suitability requirements. The correlation coefficient value should not be less than 0.995 over the concentration range. The low concentration can be excluded from the calculations if found to be below the Limit of Quantitation (s/n<10). The y-Bias is less than 0.050. The % RSD for each concentration is not more than 10.0%. The RRF for each concentration must be between 90.0% and 110.0%.

F. Determination of Impurity Relative Response FACTORS

The response factors (RF) for Ornithine and Arginine is determined at L4 and L5 concentration levels in the standard linearity study (prepared according to section (E)(2) above). The obtained response factors will be used to quantify the respective related compounds in the recovery study and the final test method.

G. Limit of Detection (LOD) and Limit of Quantitation (LOQ)

1. Preparation of LOD and LOQ Solutions

Based on the response of the 20% linearity solution (Level 1), prepare a series of dilutions in water with decreasing analyte concentration that would result in a signal to noise (S/N) ratio of between 3 and 5 for LOD and a signal to noise ratio of between 8 and 12 for LOQ.

2. Procedure

Run a system suitability and calibration test as described herein for the procedure to determine related substances/degradation products in Citrulline (this is not required if run with the linearity solutions). Inject the LOQ 6 injections, inject the LOD 3 injections and determine the S/N ratio.

3. Acceptance Criteria

The analyte concentration level that exhibits an average S/N ratio between 3 and 5 is the concentration representing the LOD. The analyte concentration level that exhibits an average S/N ratio of between 8 and 12 is the concentration representing LOQ.

H. Precision

1. Repeatability

Six sample solutions are prepared as described herein for the procedure to determine related substances/degradation products in Citrulline for sample solution preparation. Impurities of each sample are tested. The same operation continues for 3 days. Then, calculate RSD % of these 3 days to obtain day to day precision.

i. Procedure

Run a system suitability test as described herein for the procedure to determine related substances/degradation products in Citrulline. Each of the spiked solutions is then injected in duplicate, and a procedural control standard should be placed between every six injections and at the end of the sequence.

ii. Acceptance Criteria

Meet the system suitability requirements. The % difference between duplicate injections is NMT 2.0%. The RSD of the six preparations for each day should be NMT 5.0%. The overall RSD of mean assay for three days should be NMT 10%.

2. Intermediate Precision (Ruggedness)

A different chemist repeats the precision-repeatability test with the same sample by the previous chemist. Six replicate samples are prepared as described herein for the procedure to determine related substances/degradation products in Citrulline. The sample solutions are tested on different days using a different HPLC system and different column.

i. Procedure

Run a system suitability test as described herein for the procedure to determine related substances/degradation products in Citrulline. Each spiked solution is injected in duplicate and a procedural control standard should be injected following every six injections and at the end of the injection.

ii. Acceptance Criteria

Pass the system suitability requirement. Inject each solution in duplicate. The difference between duplicate injections is NMT 2.0%. The RSD of impurities assay in six samples should be NMT 10.0%. Difference between average results tested by different analyst should be NMT 10.0%.

I. Accuracy

1. Preparation of Accuracy Stock Solution

Prepare accuracy stock solution as prepared according to section (E)(1) above (Concentration: about 50.0 µg/mL each).

2. Preparation of the 50% Accuracy Samples

Pipette 5.0 mL of the stock standard solution prepared according to section (I)(1) above into 100-mL volumetric flasks, then dilute to volume with water and mix well (Concentration: about 2.5 µg/mL of each known impurity and about 2.5 µg/mL Citrulline).

3. Preparation of the 100% Accuracy Samples Pipette 10.0 mL of the stock standard solution prepared according to section (I)(1) above into 100-mL volumetric flasks, then dilute to volume with water and mix well (Concentration: about 5.0 µg/mL of each known impurity and about 5.0 µg/mL Citrulline).

4. Preparation of the 200% Accuracy Samples

Pipette 20.0 mL of the stock standard solution prepared according to section (I)(1) above into 100-mL volumetric flasks, then dilute to volume with water and mix well (Concentration: about 10.0 µg/mL of each known impurity and about 10.0 µg/mL Citrulline).

5. Procedure

Run a system suitability test as described herein for the procedure to determine related substances/degradation products in Citrulline. Make a single injection of water, a single injection of mobile phase and two injections of each of the nine Accuracy/Recovery Sample preparations. Calculate the percent area of any peak found in the retention time window of the known impurities and Citrulline from the analysis of the water blank or mobile phase, relative to the average area for the system suitability working standard injections. Calculate the µg of impurities and Citrulline spiked, the impurities and Citrulline recovered, and the percent recovered for each Accuracy/Recovery Sample. Calculate the mean recovery for each of the three levels and the % RSD.

6. Acceptance Criteria

Pass system suitability requirements. Any peak found in the retention time window of the known impurities and Citrulline from the analysis of the water blank or mobile phase is not more than 0.05%. The mean recovery of replicate preparations at each spiking level should be between 80.0% and 120.0%. The % RSD at each level must not be greater than 10.0%.

J. Range

The range of the test method from LOQ to 10 µg/mL is determined by a standard linearity study, an accuracy study and a precision study.

K. Robustness

It is a measure of the method's capability to remain unaffected by small, but deliberate variations in method parameters. The following parameters will be independently varied in this study; mobile phase flow rate, pH and organic phase composition of the mobile phase.

1. Preparation of the Standard Solution

Prepare a working standard as described herein for the procedure to determine related substances/degradation products in Citrulline.

2. Preparation of the Sample Solution

Prepare a sample solution as described herein for the procedure to determine related substances/degradation products in Citrulline.

3. Mobile Phase Flow Rate Variations

The flow rate is varied by ±0.1 mL/minute. The method flow rate of 0.8 mL/minute and at the varied flow rates of 0.7 mL/minute and 0.9 mL/minute are evaluated.

4. pH Variations

Prepare three portions of mobile phases A as the method specifies. Separately add 0.9 mL, 1.0 mL, and 1.1 mL of Acetic acid into the three portions.

5. Organic Phase Composition Variations

The organic phase composition is varied by about +2%. Prepare mobile phases B at the method specified ratio of 80% mobile phase A: 20% Methanol and at the varied ratios of 82% mobile phase A: 18% Methanol and 78% mobile phase A: 22% Methanol.

6. Procedure

Run a system suitability test as described herein for the procedure to determine related substances/degradation products in Citrulline. Repeat this sequence for the six varied conditions. Calculate the percentage of impurities found for each condition using the average area from the six system suitability standards for that condition. Evaluate the peak purity of Citrulline peak and the known impurity peaks. Calculate the Resolution between the Citrulline peak and the peak nearest to it.

7. Acceptance Criteria

Pass system suitability criteria for the method specified parameters.

L. Stability of Standard and Sample Solutions:

1. Preparation of the Sample Solution

Prepare a sample solution as described above for the procedure to determine related substances/degradation products in Citrulline, fill 6 autosampler vials, and store at room temperature for future analysis.

2. Preparation of the Mixed Known Impurities Solution

Using one of the preparations from the 100% Accuracy/Recovery samples prepared according to section (I)(3) above, fill six autosampler vials and store at room temperature for future analysis.

3. Preparation of Standard Solution

Prepare a working standard as described herein for the procedure to determine related substances/degradation products in Citrulline.

4. Procedure

Run a system suitability test as described herein for the procedure to determine related substances/degradation products in Citrulline. After one day of storage and up to seven days of storage, test the stored standard solutions on at least three days. Evaluate the stability of the stored standard solutions by quantitating the amount of Citrulline found in the stored solutions against the freshly prepared standard. Evaluate the stability of the stored known impurities solutions by quantitating the amount of known impurities found in the stored solutions against the freshly prepared standard. Evaluate the stability of the stored sample solutions by quantitating the amount of known and unknown impurities found in the stored solutions against the freshly prepared standard.

5. Acceptance Criteria

Pass system suitability requirements each analysis day. The standard solution is stable if the assay value of the stored standard solution quantitated by the freshly prepared standard solution is between 95.0% and 105.0%. The known impurities solution is stable if the difference in percent found between the known impurity values of the stored sample solution quantitated against a freshly prepared standard solution and the initial known impurity value is not more than 20.0%. The sample solution is stable if: 1) for initial impurity values greater than 25% of specification, the difference in percent found between the impurity values of the stored sample solution quantitated against a freshly prepared standard solution and the initial impurity value is not more than 20.0%; 2) for initial impurity values 25% and less, the difference in percent found between the impurity values of the stored sample solution quantitated against a freshly prepared standard solution and the initial impurity value is not more than 100.0%; and 3) any additional impurity peak (Known or Unknown) is not more than 25.0% of the proposed Specification Limit.

M. Conclusions

The method is considered validated if specificity, accuracy, linearity, precision, robustness and range results meet predefined validity & acceptance criteria.

Example II

Assays Relating to Citrulline for Injections (500 mg)

Examples of procedures to provide assays and different validation protocols have been developed relating to Citrulline for injection, (500 mg). The examples of the procedures include a method of assay of Citrulline for injection, (500 mg) and method of determination of related substances/degradation products in Citrulline for injection, (500 mg). The examples of the protocols include validation protocols for an assay method for Citrulline in an injection form, (500 mg) and related substances method validation protocols for Citrulline for injection, (500 mg).

I. Method of Assay of Citrulline, 500 mg for Injection

The objective of this example is to describe the procedure to assay Citrulline for a product of 500 mg of Citrulline for injection. The following is a brief listing and summary of parameters of the method of assay.

A. Method

The methods of determination include the Isocrated Elution, the External Standard, the Single Wavelength Detection, and Quantitation by Peak Area.

B. Equipment

The equipment used in the method includes:

HPLC with variable UV/Vis detector, auto injector and suitable data processor/recorder;

an analytical balance; and an ultrasonic bath.

C. Test Articles

Citrulline RS;

Monoammonium phosphate, AR;

Phosphoric acid, AR;

Acetonitrile, HPLC grade; and

Purified Water, graded suitable for chromatographic system.

D. Chromatographic System/Conditions

1. Column: Type: YMC-Pack Diol-120-NP

Dimensions: 4.6 mm (i.d)×25 cm

Particle Size: 5 µm

Temperature: 40° C.

2. Diluent: Water: Acetonitrile (1:1)

3. Wavelength: 200 nm

4. Injection volume: 10 µL

5. Mobile phase: Flow Rate: 2.0 mL/min

Total Run Time: 12 minutes

Mobile Phase Ammonium sodium phosphate solution (pH 2.0) (Dissolve 1.15 g of Ammonium sodium phosphate with 800 ml of water. Adjust with Phosphoric acid to a pH of 2.0. Dilute with water to 1,000 mL.):Acetonitrile=20:80. Mix well. Filter and degas.

It should be noted that the ratio of the compositions should be kept constant when preparing the mobile phase.

E. Standard Solution Preparation

Accurately weigh about 50.0 mg of Citrulline RS and transfer into a 100-mL volumetric flask. Add about 80 mL of water and sonicate with occasional shaking for 10 minutes. Allow the solution to equilibrate to room temperature and then dilute to volume with diluent and mix well. Prepare in duplicate as std-1 and std-2.

F. System Suitability Preparation (SS)

Use std-1 as system suitability solution.

G. System Suitability Test

1. The column will be equilibrated for about an hour with mobile phase. Check baseline noise and drift or any other sign of system stability. Inject 10 µL of system suitability solution when the system becomes stable.

2. Inject 10 µL of mobile phase and 10 µL of diluent. Check baseline noise and drift or any other sign of system stability. Repeat injections until the system is stable.

3. Compare the retention time (RT) to the typical RT. The typical RT is as follows:

|  | Approx. RT (min) |
| --- | --- |
| Citrulline | 7 min + 1.0 min |

Take appropriate action if there is any significant deviation from typical RT.

4. Calculate the capacity factor (k') using Citrulline peak. Take appropriate action if the capacity factor (k') is less than 2.5, or theoretical plates are less than 3,000.
5. Consecutively inject six 10 μL of std-1.
6. Calculate the mean peak area and relative standard deviation (RSD) of Citrulline from six injections of std-1.
7. Take appropriate action if RSD is more than 2.0%.

H. Calibration
1. Inject three 10 μL of std-2.
2. Calculate the mean peak area and RSD of Citrulline from three injections of std-2.
3. Take appropriate action if RSD is more than 2.0%.
4. Calculate the accuracy of std-2 against std-1.

$$\frac{A_{Std.2} \times W_{Std-1} \times 100\%}{A_{Std.1} \times W_{Std-2}} = 98.0 \sim 102.0\%$$

Where:
$A_{std.1}$=Mean peak area of Citrulline in the std-1 chromatograms
$A_{std.2}$=Mean peak area of Citrulline in the std-2 chromatograms
$W_{std.1}$=Weight of the Citrulline Reference Standard of std-1, in mg
$W_{std.2}$=Weight of the Citrulline Reference Standard of std-2, in mg Take appropriate action if recovery of std-2 is not between 98.0-102.0% when calculated using above formula.

I. Sample Solution
1. Sample Solution for Assay (Spl-1) (Prepare in Duplicate)
   a. Constitute a vial of Citrulline 500 mg for injection with 10 mL of water, shaking for 15 minutes to dissolve and mix well.
   b. Use a suitable injector to transfer all the solution in the vial into a 1,000-mL volumetric flask. Wash the injector three times with diluent and transfer all the solution from washing into the same 1,000-mL volumetric flask. Dilute to volume with diluent and mix well (Concentration: about 500 μg/mL Citrulline).

J. QUANTITATION
1. For quantitation, use peak areas of six consecutive injections of std-1. If calibration is performed just prior to sample solution injections, these results are available.
2. Inject two 10 μL of the assay sample solution (spl-1).
3. Inject 10 μL of the std-1 following every 6-12 injections to check the retention time and the peak area of Citrulline. If deviation is more than 2% when compared with the mean peak area of six system suitability injections, conduct the system suitability test again to ensure there is no carry-over from previous injections and the system is stable.

K. Calculation
Calculate the assay for each injection using the mean peak area of std-1.

$$\text{Assay \%} = \frac{A_{Spl.1} \times W_{Std.1}/100 \times P}{A_{Std.1} \times LC/10 \times 10/1000}$$

Where:
$A_{Std.1}$=Mean peak area of Citrulline in the std-1 chromatograms
$A_{Spl.1}$=Mean peak area of Citrulline in the sample solution chromatograms
$W_{Std.1}$=Weight of Citrulline RS of std-1, in mg
P=Purity of the Citrulline RS
LC=Label claim of Citrulline for Injection, in mg L. Identification
Identification is positive if the retention time of the sample corresponds to that of the standard.

II. Validation Protocol for the Assay of Citrulline, 500 mg for Injection

The objective of this protocol is to describe the procedure to validate and determine the suitability of an assay method described herein for a product of 500 mg of Citrulline for injection.

The protocol outlines a detailed validation plan for the HPLC assay test method for 500 mg of Citrulline for injection that is similar to the protocol for the assay test method for Citrulline API described above. Therefore, the protocol is not described in detail below. Summarily, the protocol validates the assay method employing High Performance Liquid Chromatography (HPLC) with Ultraviolet (UV) detection for the quantifying of Citrulline. The suitable wavelength for the detection of Citrulline is the maximum of about 200 nm. The validation of the method is accomplished by following USP/NF current guidelines for a finished product. The protocol describes the proposed experiments and acceptance criteria for the validation of the method for the determination of Citrulline in 500 mg of Citrulline for injection. The following analytical test characteristics: specificity (sample matrix interference, known impurities profile, stability-indicating studies, and forced degradation), linearity, range, precision (injection repeatability), precision (analysis repeatability), intermediate precision (ruggedness), accuracy, robustness, a filter study and the stability of solutions are be evaluated.

The known related compounds are Arginine and Ornithine. All of these compounds are both process impurities and degradation products. All the tests listed above are conducted following the assay analytical method outlined herein. USP-current, EP (Fifth Edition and supplements), ICH guidelines are used as references. The method shall be considered validated if specificity, accuracy, linearity, precision, robustness, filtration, extraction, and range results meet predefined validity & acceptance criteria.

III. Method of Determination of Related Substances/Degradation Products in Citrulline 500 mg for Injection The objective of this example is to define the procedure to determine related substances/degradation products in 500 mg of Citrulline for injection. The following is a brief listing and summary of parameters of the method.

A. Method
The methods of determination include the Gradient Method, the External Standard, the FLD Detection, and the Quantitation by Peak Area.

B. Equipment

The equipment used in the method includes:

HPLC with variable Fluorometry detector, auto injector, and suitable data processor/recorder;
one pump for reagent transport;
a reaction coil with thermostat: a column 0.25 μm (inside diameter) and 5 m in length;
an analytical balance;
an ultrasonic bath; and
a Regenerated Cellulose Membrane Filter-Agilent.

C. Test Articles

Citrulline RS (SIGMA);
Ornithine RS (SIGMA);
Arginine RS (SIGMA);
Anhydrous sodium sulfate, AR;
Sodium I-heptane sulfonate, HPLC grade;
Acetic acid, AR;
Boric acid, AR;
2-mercaptoethanol, AR;
Potassium chloride, AR;
Sodium hydroxide, AR;
O-phthalaldehyde, AR;
Ethanol, AR;
Methanol, HPLC grade; and
Purified Water, graded suitable for chromatographic system.

D. Chromatographic System/Conditions

1. Column: Type: AQ C18
   Dimensions: 4.6 mm (i.d.)×25 cm
   Particle Size: 5.0 μm
   Temperature: 20° C.
2. Diluent: water
3. Detector: Fluorometry (excitation wavelength: 340 nm, detection wavelength: 450 nm), GAIN: 8.
4. Mobile phase:
   Flow Rate: 0.8 mL/min.
   Total Run Time: 60 minutes
   Solution A: Dissolve 28.4 g of anhydrous sodium sulfate and 52 g sodium I-heptane sulfonate in 1,000 mL of water. Add 1 mL of acetic acid and mix well. Filter and degas.
   Solution B: Methanol
   Mobile phase A: solution A.
   Mobile phase B: Filter and degas a mixture of solution A and solution B at 80:20 ratio.

The chromatograph is programmed as follows:

| Time (minutes) | Solution A (%) | Solution B (%) | Flow rate (mL/min) |
|---|---|---|---|
| 0 | 100 | 0 | 0.8 |
| 6 | 100 | 0 | 0.8 |
| 8 | 0 | 100 | 0.8 |
| 40 | 0 | 100 | 0.8 |
| 41 | 100 | 0 | 0.8 |
| 50 | 100 | 0 | 0.8 |

It should be noted that the ratio of the composition should be kept constant when preparing the mobile phase.

5. Reagent: Dissolve 6.2 g boric acid, 7.4 g potassium chloride, 3.5 g sodium hydroxide in 1,000 mL of water. Add 10 mL of a solution of o-phthalaldehyde in ethanol (4 g in 25 mL) and 4 mL of 2-mercaptoethanol.
6. Reaction temperature: the reaction temperature can be maintained at a constant temperature of 30° C.
7. Flow rate of the reagent: the flow rate of the reagent can be 0.5 mL per minute.

E. Standard Solution Preparation

Accurately weigh about 100.0 mg of Citrulline RS and transfer into a 100-mL volumetric flask. Dissolve and dilute to volume with diluent to obtain a solution having a known concentration of about 1,000 μg/mL. Pipette 1.0 mL of the solution into a 200-mL volumetric flask. Dilute to volume with diluent and mix well. The concentration of Citrulline is about 5.0 μg/mL. This system suitability solution is referred to as std. in this section.

F. Resolution Solution Preparation (RS)

Accurately weigh about 10.0 mg of Citrulline RS and 10.0 mg Ornithine RS into a 100-mL volumetric flask. Dissolve and dilute to volume with diluent. Mix well to obtain a solution having a known concentration of about 100 μg/mL.

G. System Suitability Test

1. Inject 10 μL of mobile phase and 10 μL of diluent. Check baseline noise and drift or any other sign of system stability. Repeat injections until the system is stable. Note retention time of any solvent related peaks.
2. Inject 10 μL of system suitability solution.
3. Compare the retention time (RT) with the typical RTs. The typical RTs are as follows:

|  | Approx. RT (min.) |
|---|---|
| Citrulline | 5.0 ± 1.0 min. |
| Ornithine | 7.0 ± 1.0 min. |

Take appropriate action if a significant deviation from typical RT is noted.

4. Calculate the following resolution factor (R). Take appropriate action if R (between Compactin and Citrulline) is less than 5.0.
5. Calculate the column efficiency (N) using Citrulline peak. Take appropriate action if the number of theoretical plates is less than 3,000.
6. Consecutively inject six 10 μL of std.
7. Calculate the mean and RSD of Citrulline peak area from six injections of std.
8. Take appropriate action if an RSD of more than 5.0% is found.

H. Sample Solution

1. Constitute a vial of Citrulline 500 mg for injection with 10 mL of water. Shake to dissolve and mix well.
2. Accurately pipette 2.0 mL of the above solution into a 100-mL volumetric flask. Dilute to volume with water and mix well to obtain the solution at about 1,000 μg/mL.

I. Quantitation

1. For quantitation, use the results of six consecutive injections of std. If calibration is performed just prior to sample injections, these result may be used.
2. Inject two 10 μL of the sample solution preparation (spl).
3 Inject 10 μL of the standard solution every 6-12 injections to check the retention time and the peak area of Citrulline. If a deviation of more than 5.0% is found when compared to the average of six system suitability injections, conduct the system suitability test again ensuring there is no carry-over from previous injections and the system is stable.

J. Calculation

1. Quantitate known related substances using the 0.5% Citrulline standard and the appropriate response factor. The list below indicates these compounds, their retention times (RT), their relative retention (RRT) based on an RT of 5.0 minutes for Citrulline, and their relative response factors (F).

| Compound | Approx. RT (min) | RRT | F |
|---|---|---|---|
| Citrulline | 5.0 | / | / |
| Ornithine | 7.2 | 1.4 | 2.7 |
| Arginine | 18.0 | 3.6 | 1.0 |

$$\text{Related Substance} = \frac{A_{Spl} \times F \times W_{Std}/100 \text{ mL} \times 1.0 \text{ mL}/200 \text{ mL}}{A_{Std} \times LC/500} \times P$$

Where:
$A_{Std}$=Mean of peak area of Citrulline in the std chromatograms.
$A_{Spl}$=Peak area of the related compound in the sample solution chromatogram.
$W_{Std}$=Weight of the Citrulline reference standard of std, in mg.
F=Relative response factor:
P=Purity factor for the Citrulline reference standard.
LC=Label claim of Citrulline for injection, in mg
2. Calculate the total related substances and degradation products presenting, in percent using the following expression.

Ornithine %+Arginine %+Unknown–$Imp.a$%+$Imp.b$%+$Imp.c$% ... +Unknown $N$%=Total impurities %

IV. Related Substances Method Validation Protocol for Citrulline 500 mg for Injection The objective of this example is to describe the protocol to validate and demonstrate the suitability of the method of determination of substances/degradation products in 500 mg of Citrulline for injection as described herein. The protocol is similar to the protocol to validate and demonstrate the suitability of the test method of determination of related substances and degradation products of Citrulline API described above. Therefore, the protocol is not described in detail herein.

Summarily, the example validates a stability indicating assay method for the quantitation of related compounds employing post column derive method with High Performance Liquid Chromatography (HPLC) with FLD detection. The suitable excitation wavelength for the detection of Citrulline and its related compounds is 340 nm and Detection wavelength is 450 nm. PMT-Gain is 8. The validation of the method is accomplished by following USP/NF current guidelines.

The test method is used to determine two known related compounds as well as individual and total unspecified related compounds. The following studies should be conducted to make sure that the method is suitable for testing 500 mg of Citrulline for injection: system suitability, specificity (sample matrix interference, known impurities interference and stability-indicating studies), standard linearity, range, precision (injection repeatability), intermediate precision (ruggedness), accuracy, limit of detection (LOD)/limit of quantitation (LOQ), standard and sample solutions stability filtration study and robustness.

All the tests listed above are conducted following the impurities analytical method outlined herein. USP-current, EP (Fifth Edit and supplements), ICH guidelines are used as references. The method shall be considered validated and suitable if specificity, accuracy, linearity, precision, robustness, filtration and range results meet predefined validity & acceptance criteria.

Example III

Assays Relating to Citrulline Granules (5 g)

Examples of procedures to provide assays and different validation protocols have been developed relating to Citrulline granules (5 g). The examples of the procedures include a method of assay of Citrulline granules (5 g) and method of determination of related substances/degradation products of Citrulline granules (5 g). The examples of the protocols include a method validation of the assay of Citrulline granules (5 g) and method of validation of the determination of related substances/degradation products of Citrulline granules (5 g).
I. Method of Assay of Citrulline Granules, 5 g The example describes the procedure to assay Citrulline in Citrulline Granules, 5 g. The following is a brief listing and summary of at least some of the parameters of the method of assay.
A. Method The methods of determination include the Isocrated Method, the External Standard, the Single Wavelength Detection, and Quantitation by Peak Area.
B. Equipment The equipment used in the method includes:
HPLC with variable UV/Vis detector, auto injector and suitable data processor/recorder;
an analytical balance;
an ultrasonic bath; and
a regenerated cellulose membrane filter-agilent.
C. Reagents
Citrulline RS;
Monoammonium phosphate, AR;
Phosphoric acid, AR;
Acetonitrile, HPLC grade; and
Purified Water, graded suitable for chromatographic system
D. Chromatographic System/Conditions
1. Column: Type: YMC-Pack Diol-120-NP
   Dimensions: 4.6 mm (i.d.)×25 cm
   Particle Size: 5 µm
   Temperature: 40° C.
2. Diluent: Water:Acetonitrile (1:1)
3. Wavelength: 200 nm
4. Injection volume: 10 µL
5. Mobile phase: Flow Rate: 2.0 mL/min.
   Total Run Time: 12 minutes
   Ammonium sodium phosphate solution (pH 2.0) (Dissolve 1.15 g of Ammonium sodium phosphate with 800 mL of water. Adjust with Phosphoric acid to a pH of 2.0. Dilute with water to 1000 mL.):Acetonitrile=20:80. Mix well. Filter and degas.

It is noted that the ratio of the compositions should be kept constant when preparing the mobile phase.
E. Standard Solution Preparation Accurately weigh about 50.0 mg of Citrulline RS and transfer into a 100-mL volumetric flask. Add about 80 mL of water and sonicate with occasional shaking for 10 minutes.

Allow the solution to equilibrate to room temperature and then dilute to volume with diluent and mix well. Prepare in duplicate as std-1 and std-2.

F. System Suitability Preparation (SS)
Use std-1 as system suitability solution.

G. System Suitability Test
1. The column is equilibrated for about an hour with mobile phase. Check baseline noise and drift or any other sign of system stability. Inject 10 µL of system suitability solution when the system becomes stable.
2. Inject 10 µL of mobile phase and 10 µL of diluent. Check baseline noise and drift or any other sign of system stability. Repeat injections until the system is stable.
3. Compare the retention time (RT) to the typical RT. The typical RT is as follows:

|  | Approx. RT (min) |
| --- | --- |
| Citrulline | 7 min ± 1.0 min |

Take appropriate action if there is any significant deviation from typical RT.
4. Calculate the capacity factor (k') using Citrulline peak. Take appropriate action if the capacity factor (k') is less than 2.5, or theoretical plates are less than 3,000.
5. Consecutively inject six 10 µl of std-1.
6. Calculate the mean peak area and relative standard deviation (RSD) of Citrulline from six injections of std-1.
7. Take appropriate action if an RSD of more than 2.0% is found.

H. Calibration
1. Inject three 10 µL of std-2.
2. Calculate the mean peak area and RSD of Citrulline from 3 injections of std-2.
3. Take appropriate action if RSD is more than 2.0%.
4. Calculate the accuracy of std-2 against std-1.

$$\frac{A_{std-2} \times W_{std-1} \times 100\%}{A_{std-1} \times W_{std-2}} = 98.0 \sim 102.0\%$$

Where:
$A_{std-1}$=Mean peak area of Citrulline in the std-1 chromatograms
$A_{std-2}$=Mean peak area of Citrulline in the std-2 chromatograms
$W_{std-1}$=Weight of the Citrulline Reference Standard of std-1, in mg
$W_{std-2}$=Weight of the Citrulline Reference Standard of std-2, in mg
Note: Take appropriate action if recovery of std-2 is not between 98.0-102.0% when calculated using above formula.

I. Sample Solution
1. Sample Solution for Assay (spl-1) (Prepare in Duplicate)
   a. Weigh contents of 10 packs of Granules and grind them into a fine homogenous powder. Transfer an accurately weighed portion of the powder, equivalent to about 500 mg of Citrulline into a 100-mL volumetric flask.
   b. Add about 80 mL of water and sonicate with occasional shaking for 15 minutes. Allow the solution to equilibrate to room temperature and then dilute to volume with water and mix well,
   c. Filter about a 20-mL portion of the sample through a 0.45 µm Agilent Regenerated Cellulose Filter into a suitable container after discarding the first 3 mL.
   d. Accurately pipette 10.0 mL of the filtered solution into a 100-mL volumetric flask. Dilute to volume with diluent.
   It should be noted that the standard and sample solutions may be used for up to 48 hours.

J. Quantitation
1. For quantitation, use the results of six consecutive injections of std-1. If calibration is performed just prior to sample injections, these result may be used.
2. Inject two 10 µL of the assay sample solution (spl-1).
3. Inject 10 µL of the content uniformity sample solution (spl-2).
4. Inject 10 µL of the standard solution 1 (std-1) every 6-12 injections to check the retention time and the peak area of Citrulline. If deviation is more than 2.0% when compared to the average of six system suitability injections, conduct the system suitability test again to ensure there is no carry-over from previous injections and to ensure the system is stable.

K. Calculation
Assay Calculation:
Calculate the potency for each injection using the mean of the peak area of std-1.

$$\text{Assay \%} = \frac{A_{Spl.1} \times W_{Std.1}/100 \text{ mL} \times P}{A_{Std.1} \times W_{Spl.1}/100 \text{ mL} \times 10.0 \text{ mL}/100 \text{ mL} \times LC/Wa}$$

Where:
$A_{Std.1}$=Mean peak area of Citrulline in the std-1 chromatograms
$A_{Spl.1}$=Mean peak area of Citrulline in the sample solution chromatograms
$W_{Std.1}$=Weight of the Citrulline RS of std-1, in mg
$W_{Std.1}$=Mean content of 20 Citruiline Granule, in mg
P=Purity of the Citrulline reference standard
LC=Label claim of Citrulline, in mg/granule L. Identification
Identification is positive if the retention time of the sample corresponds to that of the standard.

II. Validation Protocol for Method of Assay of Citrulline Granules, 5 g

The example describes the protocol to validate and determinate the suitability of the assay method described herein for the product of Citrulline granules.

The example outlines a detailed validation plan for the HPLC assay test method for Citrulline granules that is similar to the protocol for the assay test method for Citrulline API described above. Therefore, the protocol is not described in detail below. Summarily, the example validates the assay method employing High Performance Liquid Chromatography (HPLC) with Ultraviolet (UV) detection for the quantitation of Citrulline. The suitable wavelength for the detection of Citrulline is the maximum of about 200 nm. The validation of the method is accomplished by following USP/NF current guidelines for finished product. The following analytical test characteristics: specificity (sample matrix interference, placebo interference, known impurities interference, stability-indicating studies, and forced degradation), linearity and range, precision (repeatability), precision (analysis repeatability), intermediate precision (ruggedness), accuracy, robustness, a filter study and the stability of solutions are evaluated.

The known related compounds are Arginine and Ornithine. These compounds are both process impurities and degradation products. The tests listed above are conducted following the assay analytical method outlined herein. USP-current, EP (Fifth Edition and supplements), ICH guidelines are used as references. The method shall be considered validated if specificity, accuracy, linearity, precision, robustness, filtration, extraction and range results meet predefined validity & acceptance criteria.

III. Method of Determination of Related Substances/Degradation Products in Citrulline Granules, 5.0 g The objective of this example is to define the procedure to determine related substances/degradation products in Citrulline granules. The following is a brief listing and summary of parameters of the method.

A. Method

The methods of determination include the Gradient Method, the External Standard, the FLD Detection, and the Quantitation by Peak Area.

B. Equipment

The equipment used in the method includes:

HPLC with variable Fluorometry detector, auto injector, and suitable data processor/recorder;

one pump for reagent transport;

a reaction coil with thermostat: a column 0.25 µm (inside diameter) and 5 m in length;

an analytical balance;

an ultrasonic bath; and a Regenerated Cellulose Membrane Filter-Agilent.

C. Test Articles

Citrulline RS (SIGMA);
Ornithine RS (SIGMA);
Arginine RS (SIGMA);
Anhydrous sodium sulfate, AR;
Sodium I-heptane sulfonate, HPLC grade;
Acetic acid, AR;
Boric acid, AR;
2-mercaptoethanol, AR;
Potassium chloride, AR;
Sodium hydroxide, AR;
O-phthalaldehyde, AR;
Ethanol, AR;
Methanol, HPLC grade; and
Purified Water, graded suitable for chromatographic system D. Chromatographic System/Conditions 1 Column: Type: AQ C18
Dimensions: 4.6 mm (i.d.)×25 cm
Particle Size: 5.0 µm
Temperature: 20° C.

2. Diluent: water

3. Detector: Fluorometry (excitation wavelength: 340 nm, detection wavelength: 450 nm), GAIN: 8

4. Mobile phase: Flow Rate: 0.8 mL/min.
Total Run Time: 60 minutes
Solution A: Dissolve 28.4 g of anhydrous sodium sulfate and 5.2 g sodium I-heptane sulfonate in 1,000 mL of water. Add 1 mL of acetic acid. Mix well. Filter and degas.
Solution B: Methanol
Mobile phase A: Solution A
Mobile phase B: Filter and degas a mixture of Solution A and Solution B at 80:20 ratio.

The chromatograph is programmed as follows:

| Time (minutes) | Solution A (%) | Solution B (%) | Flow rate (mL/min) |
|---|---|---|---|
| 0 | 100 | 0 | 0.8 |
| 6 | 100 | 0 | 0.8 |
| 8 | 0 | 100 | 0.8 |
| 40 | 0 | 100 | 0.8 |
| 41 | 100 | 0 | 0.8 |
| 50 | 100 | 0 | 0.8 |

Note: Keep the ratio of the compositions constant when preparing the mobile phase.

5. Reagent: Dissolve 6.2 g boric acid, 7.4 g potassium chloride, 3.5 g sodium hydroxide in 1,000 mL of water. Add 10 mL of a solution of o-phthalaldehyde in ethanol (4 g in 25 mL) and 4 mL of 2-mercaptoethanol.

6. Reaction temperature: A constant temperature of 30° C.

7. Flow rate of the reagent: 0.5 mL per minute.

E. Standard Solution Preparation

Weigh accurately about 100.0 mg of Citrulline RS. Transfer into a 100-mL volumetric flask. Dissolve and dilute to volume with diluent to obtain a solution having a known concentration of about 1,000 µg/mL. Pipette 1.0 mL of the solution into a 200-mL volumetric flask. Dilute to volume with diluent and mix well. The concentration of Citrulline is about 5.0 µg/mL. The resulting solution will be referred to as std. in this section.

F. Resolution Solution Preparation (RS)

Weigh accurately about 10.0 mg of Citrulline RS and 10.0 mg Ornithine RS each into a 100-mL volumetric flask. Dissolve and dilute to volume with diluent. Mix well to obtain a solution having a known concentration of about 100 µg/mL. This solution is the system suitability solution.

G. System Suitability Test

1. Inject 10 µL of mobile phase and 10 µL of diluent. Check baseline noise and drift or any other sign of system stability. Repeat injections until the system is stable. Note retention time of any solvent related peaks.

2. Inject 10 µL of system suitability solution.

3. Compare the retention time (RT) to the typical RT. The typical RT is as follows:

|  | Approx. RT (min) |
|---|---|
| Citrulline | 5.0 ± 1.0 min |
| Ornithine | 7.0 ± 1.0 min |

Take appropriate action if a significant deviation from typical RT is noted.

4. Calculate the following resolution factor (R). Take appropriate action if R (between Compactin and Citrulline) is less than 5.0.

5. Calculate the column efficiency (N) using Citrulline peak. Take appropriate action if the number of theoretical plates is less than 3,000.

6. Consecutively inject six 10 µL of std.

7. Calculate the mean and relative standard deviation (RSD) of Citrulline peak area from six injections of std.

8. Take appropriate action if an RSD of more than 5.0% is found.

H. Sample Solution

1. Weigh and finely powder contents of 10 packs. Transfer an accurately weighed portion of the powder, equivalent to about 100 mg of Citrulline to a 100-mL volumetric flask.

2. Add about 50 mL of water and sonicate for 15 minutes with occasional shaking. Allow the solution to equilibrate to room temperature and then dilute to volume with water and mix well. Pass the solution through a 0.45 μm filter membrane. Filter a portion into autosampler vials after discarding the first 5 mL of the filtrate.

I. Quantitation
1. For quantitation, use the results of six consecutive injections of std. If calibration is performed just prior to sample injections, these result may be used.
2 Inject 10 μL of the sample solution preparation (spl) in duplicate.
3. Inject 10 μL of the standard solution every 6-12 injections to check the retention time and the peak area of Citrulline. If a deviation of more than 5.0% is found when compared to the average of 6 system suitability injections, conduct the system suitability test again ensuring there is no carry-over from previous injections and the system is stable.

J. Calculation
1. Quantitate known related substances using the 0.5% Citrulline standard and the appropriate response factor. The list below indicates these compounds, their retention times (RT), their relative retention (RRT) based on an RT of 5.0 minutes for Citrulline, and their relative response factors (F).

| Compound | Approx. RT (min.) | RRT | F |
|---|---|---|---|
| Citrulline | 5.0 | / | / |
| Ornithine | 7.2 | 1.4 | 2.7 |
| Arginine | 18.0 | 3.6 | 1.0 |

$$\text{Related Substance} = \frac{A_{Spl} \times F \times W_{Std}/100 \text{ mL} \times 1.0 \text{ mL}/200 \text{ mL} \times P}{A_{Std} \times W_{Spl}/100 \text{ mL} \times LC/Wa} \times 100$$

Where:
$A_{Std}$=Mean peak area of Citrulline in the std chromatograms
$A_{Spl}$=Peak area of the related compound in the sample solution chromatogram
$W_{Std}$=Weight of the Citrulline Reference Standard of std, in mg
$W_{Spl}$=Weight of the Citrulline granules powder, in mg
F=Relative Response factor
P=Purity of the Citrulline Reference Standard
LC=Label claim of Citrulline, in mg/pack
Wa=Mean content of 10 Citrulline Granules, in mg 2. Calculate the total related substances and degradation products presenting, in percent using the following expression:

Ornithine %+Arginine %+Unknown–*Imp.a*%+*Imp.b*%+*Imp.c*% . . . +Unknown *N*%=Total impurities %

IV. Related Substances Method Validation Protocol for Citrulline Granules, 5.0 g The objective of this example is to describe the protocol to validate and demonstrate the suitability of method of determination of substances/degradation products in 5.0 g of Citrulline granules described herein. The protocol is similar to the protocol to validate and demonstrate the suitability of the test method of determination of related substances and degradation products of Citrulline API described above. Therefore, the protocol is not described in detail herein.

Summarily, the example protocol validates a Stability Indicating assay method for the quantitation of related compounds employing post column derive method with High Performance Liquid Chromatography (HPLC) with FLD detection. The suitable excitation wavelength for the detection of Citrulline and its related compounds is 340 nm and Detection wavelength is 450 nm. PMT-Gain is 8. The validation of the method is accomplished by following USP/NF current guidelines.

This test method is used to determine 2 known related compounds as well as individual and unspecified related compounds.

The following studies are conducted to make sure that the method is suitable for testing the 5.0 g of Citrulline granules: system suitability, specificity (sample matrix interference, known impurities interference and stability-indicating studies), standard linearity, accuracy, range, precision (repeatability), intermediate precision (ruggedness), accuracy, limit of detection (LOD)/limit of quantitation (LOQ), standard and sample solutions stability, filtration and robustness.

All the tests listed above are conducted following the impurities analytical method outlined herein. USP-current, EP (Fifth Edit and supplements), ICH guidelines are used as references.

The method shall be considered validated and suitable if specificity, accuracy, linearity, precision, robustness, filtration and range results meet predefined validity & acceptance criteria.

Example IV

Assays Relating to Citrulline Chewable Tablets (500 mg)

Examples of procedures to provide assays and different validation protocols have been developed relating to Citrulline chewable tablets (500 mg). The examples of the procedures include a method of assay of Citrulline chewable tablets (500 mg), method of dissolution of Citrulline chewable tablets (500 mg), and method of determination of related substances/degradation products of Citrulline chewable tablets (500 mg). The examples of the protocols include a validation method of the assay of Citrulline chewable tablets (500 mg), validation method of the dissolution of Citrulline chewable tablets (500 mg), and validation method of the determination of related substances/degradation products of Citrulline chewable tablets (500 mg).

I. Method of Assay of Citrulline Chewable Tablets, 500 mg

An objective of this example is to define the procedure to assay Citrulline in Citrulline Chewable Tablets (500 mg). The following is a brief listing and summary of at least some of the parameters of the method of assay.

A. Method
The methods of determination include the Isocrated Method, the External Standard, the Single Wavelength Detection, and Quantitation by Peak Area.

B. Equipment
The equipment used in the method includes:
HPLC with variable UV/Vis detector, auto injector and suitable data processor/recorder;
an analytical balance;
an ultrasonic bath; and
a regenerated cellulose membrane filter-agilent.

C. Reagents
- Citrulline RS;
- Monoammonium phosphate, AR;
- Phosphoric acid, AR;
- Acetonitrile, HPLC grade; and
- Purified Water, graded suitable for chromatographic system D. Chromatographic System/Conditions
1. Column: Type: YMC-Pack Diol-120-NP
   Dimensions: 4.6 mm (i.d.)×25 cm
   Particle Size: 5 μm
   Temperature: 40° C.
2. Diluent: Water: Acetonitrile (1:1)
3. Wavelength: 200 nm
4. Injection volume: 10 μL
5. Mobile phase: Flow Rate: 2.0 mL/min.
   Total Run Time: 12 minutes
   Ammonium sodium phosphate solution (pH2.0) (Dissolve 1.15 g of Ammonium sodium phosphate with 800 mL of water. Adjust with Phosphoric acid to a pH of 2.0. Dilute with water to 1,000 mL.): Acetonitrile=20:80. Mix well. Filter and degas.

Note: Keep the ratio of the compositions constant when preparing the mobile phase.

E. Standard Solution Preparation

Accurately weigh about 50.0 mg of Citrulline RS and transfer into a 100-mL volumetric flask. Add about 80 mL of water and sonicate with occasional shaking for 10 minutes. Allow the solution to equilibrate to room temperature and then dilute to volume with diluent and mix well. Prepare in duplicate as std-1 and std-2.

F. System Suitability Preparation

Use std-1 as system suitability solution.

G. System Suitability Test
1. The column will be equilibrated for about an hour with mobile phase. Check baseline noise and drift or any other sign of system stability. Inject 10 μL of system suitability solution when the system becomes stable.
2. Inject 10 μL of mobile phase and 10 μL of diluent. Check baseline noise and drift or any other sign of system stability. Repeat injections until the system is stable.
3. Compare the retention time (RT) to the typical RT. The typical RT is as follows:

|  | Approx. RT (min) |
| --- | --- |
| Citrulline | 7 min ± 1.0 min |

Take appropriate action if there is any significant deviation from typical RT.

4. Calculate the capacity factor (k') using Citrulline peak. Take appropriate action if the capacity factor (k') is less than 2.5, or theoretical plates are less than 2,000.
5. Consecutively inject six 10 μL of std-1.
6. Calculate the mean peak area and relative standard deviation (RSD) of Citrulline from six injections of std-1.
7. Take appropriate action if RSD is more than 2.0%.

H. Calibration
1. Inject three 10 μL of std-2.
2. Calculate the mean peak area and RSD of Citrulline from three injections of std-2.
3. Take appropriate action if RSD is more than 2.0%.
4. Calculate the accuracy of std-2 against std-1.

$$\frac{A_{std-2} \times W_{std-1} \times 100\%}{A_{std-1} \times W_{std-2}} = 98.0 \sim 102.0\%$$

Where:
- $A_{std-1}$=Mean peak area of Citrulline in the std-1 chromatograms
- $A_{std-2}$=Mean peak area of Citrulline in the std-2 chromatograms
- $W_{std-1}$=Weight of the Citrulline Reference Standard of std-1, in mg
- $W_{std-2}$=Weight of the Citrulline Reference Standard of std-2, in mg Note: Take appropriate action if recovery of std-2 is not between 98.0-102.0% when calculated using above formula.

I. Sample Solution
1. Sample Solution for Assay (spl-1) (Prepare in Duplicate)
   a. Weigh 20 tablets of Chewable Tablets and grind them into fine homogenous powder. Transfer an accurately weighed portion of the powder, equivalent to about 500 mg of Citrulline into a 100-mL volumetric flask.
   b. Add about 80 mL of water and sonicate with occasional shaking for 15 minutes. Allow the solution to equilibrate to room temperature and then dilute to volume with water and mix well.
   c. Filter about a 20-mL portion of the sample through a 0.45 μm Agilent Regenerated Cellulose Filter into a suitable container after discarding the first 3 mL.
   d. Accurately pipette 10.0 mL of the filtered solution into a 100-mL volumetric flask. Dilute to volume with diluent.
2. Sample Solution for Content Uniformity (spl-2)
   a. Separately place ten tablets into ten 200-mL volumetric flasks. Add about 100 mL of water and sonicate with occasional shaking until tablets disintegrate completely. Equilibrate to room temperature and dilute with diluent to volume. Mix well.
   b. Filter about a 20-mL portion of the sample through a 0.45 μm Agilent Regenerated Cellulose Filter into a suitable container after discarding the first 3 mL.
   c. Accurately pipette 10.0 mL of the filtered solution into a 50-mL volumetric Flask. Dilute to volume with diluent.

Note: The standard and sample solutions may be used for up to 48 hours.

J. Quantitation
1. For quantitation, use the results of six consecutive injections of std-1. If calibration is performed just prior to sample injections, the result may be used.
2. Inject two 10 μL of the assay sample solution (spl-1).
3. Inject 10 μL of the content uniformity sample solution (spl-2).
4. Inject 10 μL of std-1 every 6-12 injections to check the retention time and the peak area of Citrulline. If deviation is more than 2.0% when compared with the average of six system suitability injections, conduct the system suitability test again to ensure there is no carry-over from previous injections and the system is stable.

K. Calculation
1. Assay:
Calculate the potency for each injection using the mean of peak area of std-1.

$$\text{Assay \%} = \frac{A_{spl.1} \times W_{std.1}/100 \text{ mL} \times P}{A_{std.1} \times W_{spl.1}/100 \text{ mL} \times 10.0 \text{ mL}/100 \text{ ml} \times LC/W_a}$$

Where:
$A_{std.1}$=Mean peak area of Citrulline in the std-1 chromatograms
$A_{spl.1}$=Mean peak area of Citrulline in the sample solution chromatograms
$W_{std.1}$=Weight of the Citrulline Reference Standard (RS) of std-1, in mg
$W_{Spl.1}$=Weight of Citrulline in the sample, in mg
$W_a$=Mean content of 20 Citrulline Chewable Tablets, in mg
P=Purity of the Citrulline RS
LC=Label claim of Citrulline, in mg/tablet
2. Content Uniformity.
Calculation the potency for each injection using the mean peak area of Std-1.

$$\% \text{ of claim} = \frac{A_{spl.2} \times W_{std.1}/100 \text{ mL} \times P}{A_{std.1} \times LC/200 \text{ mL} \times 10.0 \text{ mL}/50 \text{ mL}}$$

Where:
$A_{std.1}$=Mean peak area of Citrulline in the std-1 chromatogram
$A_{spl.2}$=Mean peak area of Citrulline in the sample solution chromatogram
$W_{std.1}$=Weight of the Citrulline RS of std-1, in mg
P=Purity of the Citrulline RS
LC=Label claim of Citrulline, in mg/tablet
L. Identification
Identification is positive if the retention time of the sample corresponds to that of the standard.
II. Validation Protocols of the Assay of Citrulline Chewable Tablets, 500 mg
An objective of this example is to describe the procedure to validate and demonstrate the suitability of the assay method described herein for a product of Citrulline used in Chewable Tablets. The protocol is similar to the protocol for the assay test method for Citrulline API described above. Therefore, the protocol is not described in detail below.

Summarily, the example protocol validates the assay method employing High Performance Liquid Chromatography (HPLC) with Ultraviolet (UV) detection for the quantitation of Citrulline. The suitable wavelength for the detection of Citrulline is the maximum of about 200 nm. The validation of the method will be accomplished by following USP/NF current guidelines for finished product. The protocol describes in detail experiments and acceptance criteria for the validation of the method for the determination of Citrulline in Chewable Tablets. The following analytical test characteristics: specificity (sample matrix interference, placebo interference, known impurities interference, stability-indicating studies and forced degradation), linearity, range, precision (repeatability), precision (analysis repeatability), intermediate precision (ruggedness), accuracy, robustness, a filter study and the stability of solutions will be evaluated.

The known related compounds are Arginine and Ornithine. All of these compounds are both process impurities and degradation products. All the tests listed above are conducted following the assay analytical method outlined herein. USP-current, EP (Fifth Edit and supplements), ICH guidelines are used as references. The method shall be considered validated if specificity, accuracy, linearity, precision, robustness, filtration, extraction, and range results meet predefined validity & acceptance criteria.

III. Method of Dissolution of Citrulline Chewable Tablets, 500 MG

The objective of this example is to describe a procedure to determine a dissolution test in Citrulline Chewable tablets. The following is a brief listing and summary of at least some of the parameters of the method.

A. Method
The methods of determination include:
Paddle;
Isocratic Method;
External Standard;
Single Wavelength Detection; and
Quantitation by Peak Area.
B. Equipment
The equipment used in the method includes:
HPLC with variable UV/Vis detector, auto injector, and suitable data processor/recorder;
Analytical balance;
Ultrasonic bath;
Dissolution Apparatus;
Water degassing instrument; and
Regenerated Cellulose Membrane Filter-Agilent.
C. Test Article
Citrulline RS (reference standard);
Monoammonium phosphate, AR;
Phosphoric acid, AR;
Acetonitrile, HPLC grade; and
Purified Water, graded suitable for chromatographic system.
D. Dissolution System/Condition
Dissolution Medium: water
Apparatus: Paddle
Speed: 75 rpm/min.
Temperature: 37±0.5° C.
Sample Times: 5, 10, 15, 20, 30, 45, 60 and 90 minutes (dissolution profile)
Sample Time: 45 minutes (single point)
Sample Volume: 10 mL
Dissolution Volume: 900 mL
E. Chromatographic System/Conditions
1. Column: Type: YMC-Pack Diol-120-NP
Dimensions: 4.6 mm (i.d.)×25 cm
Particle Size: 5 µm
Temperature: 40° C.
2. Diluent: Acetonitrile
3. Wavelength: 200 nm
4. Injection volume: 10 µL
5. Mobile phase: Flow Rate: 2.0 mL/min.
Total Run Time: 12 minutes
Mobile Phase Preparation: Ammonium sodium phosphate solution (pH2.0) (Dissolve 1.115 g of Ammonium sodium phosphate in 800 mL of water. Adjust with Phosphoric acid to a pH of 2.0. Dilute with water to 1,000 mL.): Acetonitrile=20:80. Mix, filter and degas.

Note: Keep the ratio of the compositions constant when preparing the mobile phase.

F. Standard Solution Preparation

Accurately weigh about 27.8 mg of Citrulline RS, transfer into a 100-mL volumetric flask. Dissolve and dilute to volume with water:acetonitrile (1:1) and mix well. The resulting solution will be referred to as std. in this section.

G. System Suitability Solution Preparation

Use std. as system suitability solution.

H. System Suitability Test

1. The column will be equilibrated for about an hour with mobile phase. Check baseline noise and drift or any other sign of system instability. Inject 10 μL of system suitability solution when the system becomes stable.
2. Inject 10 μL of mobile phase. Inject 10 μL of diluent. Check baseline noise and drift or any other sign of system instability. Repeat injections until the system is stable.
3. Compare the retention time (RT) to the typical RT. The typical values is as follows:

|  | Approx, RT (min) |
| --- | --- |
| Citrulline | 7 min + 1.0 min |

Take appropriate action if there is any significant deviation from typical value, 4. Calculate the capacity factor (k') using Citrulline peak. Take appropriate action if the capacity factor (k) less than 25, or theoretical plates are less than 2,000.
5. Consecutively inject six 10 μL of std-1.
6. Calculate the mean peak area and relative standard deviation (RSD) of Citrulline from six std-1 injections.
7. Take appropriate action if RSD is more than 2.0%.

I. Set-Up of Dissolution Method

1. Set-Up of Dissolution Apparatus:
   a. Pour 900 mL of the dissolution medium into each of the dissolution chambers. Allow temperature to stabilize at 37±0.5° C.
   b. Set paddle at 2.5 cm from the bottom of the chambers.
   c. Introduce sampling probes into the chambers to depth so that the samples will be taken from mid point between the top of the paddle and the surface of the dissolution medium.
   d. Set stirring speed at 75 rpm.
2. Sample Preparation: (spl.)

Perform on six individual tablets at the same time,
   a. Drop six tablets into six dissolution chambers. Start rotating timing simultaneously.
   b. Single point: Take 10 mL samples after 75 minutes.
   c. Dissolution profile: Take 10.0 mL samples after 5, 10, 15, 20, 30, 45 and 60 minutes. Add 10.0 mL dissolution medium into every dissolution chamber at the end of every sampling. Adjust the stirring speed to 200 rpm, take 10 mL sample at 90 minutes.
   d. Filter the sample solution through a 0.45 μm Regenerated Cellulose Membrane Filter (Agilent), after discarding at least the first 3 mL of filtrate. Pipette accurately 5.0 mL of the filtered solution into a 10-mL volumetric flask, dilute to volume with diluent, and mix well.

Note: The standard and sample solutions may be used for up to 48 hours.

J. Quantitation

1. For quantitation, use the results of six consecutive injections of std.
2. Inject one 10 μL of the sample solution preparation (spl.).
3. Inject 10 μL of the standard solution every 6-12 injections to check the retention time and the peak area of Citrulline. If a deviation of more than 2.0% is found when compared to the average of six system suitability injections, conduct the system suitability test again ensuring there is no carry-over from previous injections and the system is stable.

K. Calculation

Calculate % dissolved for each of the samples taken using peak areas. Calculate the mean and the RSD of std. Report the single point (45 min.) dissolved rate and the dissolution profile (5 min., 10 min., 15 min., 20 min., 30 min., 45 min., 60 min., 90 min.).

$$\% \text{ Citrulline Dissolved} = \frac{\left(a + \sum_{i=1}^{n} ai \times V1/V2\right) \times W_{std.}/100 \text{ mL} \times P}{A_{std.} \times LC/V2 \times 5.0 \text{ ml}/10 \text{ ml}}$$

Where:

$A_{Std.}$=Mean of peak area of Citrulline in the std. chromatogram a=Peak area of Tacrolimus in the sample solution chromatogram at time t $\sum_{i=1}^{n} ai$ = Total peak area of Citrulline in the sample solution chromatogram before time $t$ V1=The volume of sample V2=The volume of medium $W_{Std}$=Weight of the Citrulline Reference Standard of std, in mg P=Purity factor for the Citrulline Reference Standard LC=Label claim of Citrulline, in mg/tablet IV. Validation Protocols for the Dissolution of Citrulline Chewable Tablets, 500 MG The objective of this example is to provide a validation plan for the dissolution test method for the finished product of Citrulline chewable tablets (500 mg).

This example validates the dissolution method employing a HPLC with Ultraviolet (UV) detection at the maximum of about 200 nm for the quantitation of Citrulline. The validation of the method is accomplished by following USP/NF current guidelines for finished pharmaceuticals. The protocol describes in detail the proposed experiments and acceptance criteria for the validation of the method for the Citrulline chewable Tablets. The following analytical test characteristics: specificity, linearity and range, method precision (repeatability) and intermediate precision (ruggedness), robustness, the stability of analytical solutions, and a filter study are evaluated.

The dissolution sample concentration is 277.8 μg/mL (100% released), and the working standard concentration is accordingly 277.8 μg/mL. All the tests listed above are conducted following the assay analytical method outlined herein.

EP (2005 and supplements), ICH guidelines, China Pharmacopoeia 2005 addendum, USP-current guidelines are used as references.

A. Method Set Up

1. Dissolution System/Condition

| | |
|---|---|
| Dissolution Medium: | water |
| Apparatus: | Paddle |
| Speed: | 75 rpm/min. |
| Temperature: | 37 ± 0.5° C. |
| Sample Times: | 5, 10, 15, 20, 30, 45, 60 and 90 minutes (dissolution profile) |
| Sample Time: | 45 minutes (single point) |
| Sample Volume: | 10 mL |
| Dissolution Volume: | 900 mL |

2. Chromatographic System and Parameters

| | |
|---|---|
| Pump: | Agilent 1200 |
| Detector: | Agilent 1200 |
| Auto sampler: | Agilent 1200 |
| Column: | YMC-Pack Diol-120-NP Dimensions 250 mm × 4.6 mm (ID), particle size: 5.0 μm |
| Column Temperature: | 40° C. |
| Mobile Phase: | Buffer: Acetonitrile (1:4) |
| Flow Rate: | 2.0 mL/min. |
| Injection Volume: | 10 μL |
| Detector & Wavelength: | UV at 200 nm |
| Run Time: | 12 minutes or as appropriate |

3. Materials
Citrulline RS
Citruiline Chewable Tablets
Arginine
Ornithine

4. Reagents

| | |
|---|---|
| Acetonitrile | HPLC Grade |
| Water | De-ionized |
| Ammonium sodium phosphate | A.R. Reagent |
| Phosphoric acid | A.R. Reagent |
| Hydrochloric Acid (HCl), (36.5-38.0%) | A.R. Reagent |
| Sodium Hydroxide (NaOH) | A.R. Reagent |
| Hydrogen Peroxide, 30% ($H_2O_2$) | A.R. Reagent |

5. Preparation of the Ammonium Sodium Phosphate Solution (pH2.0)

Dissolve 1.15 g of ammonium sodium phosphate in 800 mL of water. Adjust with phosphoric acid to a pH of 2.0. Dilute with water to 1,000 mL and mix well.

6. Preparation of the Mobile Phase

In a suitable flask, prepare a 1:4 mixture of ammonium sodium phosphate solution (pH 2.0) and Acetonitrile (v/v) and then filter through a 0.45 μm Econofilter and degas prior to use.

Note: do not degas for an extended period of time since evaporation of the organic solvent may alter the characteristics of the chromatographic system.

7. Preparation of the Diluent

In a suitable flask, prepare a 1:1 mixture of water and Acetonitrile (v/v).

8. Preparation of Standard Solutions

Weigh accurately about 27.8 mg of Citrulline RS and transfer into a 100-mL volumetric flask. Add about 80 mL of diluent and sonicate with occasional shaking for 10 minutes. Allow the solution to equilibrate to room temperature and then dilute to volume with diluent and mix well to obtain a standard solution having a known concentration of about 278 μg/mL.

9. Preparation of the Dissolution Sample Solutions i. Preparation of the Dissolution Stock Sample Solutions After completion of the dissolution time period, carefully withdraw 10 mL of the solution as described herein under the procedure for the dissolution test for Citrulline chewable tablets using a disposable plastic syringe. Filter through a 0.45 μm Regenerated Cellulose Membrane Filter (Agilent) membrane filter and collect the filtrate after discarding the initial 3 mL of the filtrate to saturate the filter and collect the filtrate in a suitable container.

ii. Preparation of the Dissolution Working Sample Solution:

Pipette accurately 5 mL of the filtrate into a 10-mL volumetric flask, add acetonitrile to volume and mix well.

B. System Suitability

The system suitability test is conducted as required by the test method. The column is equilibrated for about an hour prior to injection of the system suitability solution. The resolution solution and standard solution are used for the system suitability. After the chromatographic system is equilibrated, one injection of the system solution (standard solution) and another five injections of the standard solution are performed. The precision (RSD), tailing factor (T), capacity factor (k'), and theoretical plates (N) are calculated.

Acceptance criteria:
Precision (RSD): NMT 2.0% (Citrulline)
Theoretical plates (N): NLT 2000 (Citrulline)
Capacity factor (k') NLT 2.5 (Citrulline)
Tailing Factor (T): NMT 2.0 (Citrulline)

C. Specificity

1. Dissolution Medium Interference

Water can be used as the dissolution medium interference.

2. Placebo Interference (1×)

Weigh a portion of the placebo blend equivalent to the Citrulline chewable tablets formulation and transfer to a dissolution vessel (only one vessel). Rotate the paddles at 200 RPM for about 45 minutes (in order to dissolved completely). Prepare placebo (1×) solution for each formulation following the instructions of the procedure for the dissolution test for Citrulline chewable tablets.

3. Placebo Interference (3×)

Weigh a portion of the placebo blend equivalent to twice the Citrulline chewable tablets formulation and transfer to a dissolution vessel (only one vessel). Rotate the paddles at 200 RPM for about 45 minutes. Prepare placebo (1×) solution for each formulation following the instructions of the procedure for the dissolution test for Citrulline chewable tablets.

4. Procedure:

Read the samples as described in ARD-FPTM031C.

Injection Sequence:

| | | |
|---|---|---|
| Mobile phase | 1 injection | 30 minutes |
| Diluent | 1 injection | 30 minutes |
| Standard | 6 injections | 12 minutes |
| Placebo at the WC | 1 injection | 30 minutes |
| Placebo at 3 × WC | 1 injection | 30 minutes |
| Control sample solution | 1 injection | 30 minutes |

The chromatograms should be plotted at attenuation corresponding to full scale of the respective active peak. In addition, the chromatograms should be re-plotted with more sensitive attenuation to allow better examination for possible interference.

Validity Criteria:

Meet system suitability requirements.

Acceptance Criteria:

Any peak found in the retention time window of Citrulline in the chromatograms of the diluent and placebo solutions is NMT 0.5%.

The spectral purity of Citrulline peak in the chromatograms of the control sample should be greater than 990.

Any peaks in the chromatograms of the control sample must show a resolution NLT 1.5.

D. Standard Linearity

The working concentration for 500 mg strength tablets is about 277.8 µg/mL (100% released). The linearity study is designed to cover the range from 10% to 120% of the working concentration.

1. Citrulline Standard Solution

Prepare the standard solution using the same procedure as described in the procedure for the dissolution test for Citrulline chewable tablets.

2. Preparation of the Citrulline Stock Solution:

Weigh out accurately about 550 mg of Citrulline RS and transfer into a 100-mL volumetric flask. Add about 80 mL of diluent and sonicate with occasional shaking for 10 minutes. Allow the solution to equilibrate to room temperature and then dilute to volume with diluent and mix well to obtain a solution having a known concentration of about 5.50 mg/mL. This is the Linearity Stock Solution.

3. Preparation of the Linearity Solutions:

Use the "Citrulline Stock Solution" to prepare the linearity solutions as shown in the table below. Dilute to volume with Acetonitrile: water (1:1), mix well and label appropriately.

| Linearity Solution | Nominal Conc. Citrulline (µg/mL) | Volume Pipetted (mL) | Vol. Flask Volume (mL) |
|---|---|---|---|
| L1 (10%) | 27.5 | 1 | 200 |
| L2 (20%) | 55.0 | 2 | 200 |
| L3 (30%) | 82.5 | 3 | 200 |
| L4 (50%) | 137.5 | 5 | 200 |
| L5 (80%) | 220 | 4 | 100 |
| L6 (100%) | 275 | 5 | 100 |
| L7 (120%) | 330 | 6 | 100 |

4. Chromatographic System and Procedure

Establish the system suitability as described in the procedure for the dissolution test for Citrulline chewable tablets. Each of the sample solutions are injected in duplicate and a procedural control standard should be placed between every six injections and at the end of the sequence.

Analyze the linearity study as follows:

1. Plot the peak area vs. concentration.

2. Perform linear regression analysis and determine the slope, y-intercept and correlation coefficient (R).

3. Calculate the mean response factors (MRF), relative to the relative mean response factor of the corresponding 100% solution (L6 linearity solution).

4. Plot the relative mean response factors versus concentration.

Validity Criteria:

Meet system suitability requirements.

The % difference between duplicate injections is within ±2%.

The procedural controls meet criteria.

Acceptance Criteria:

Correlation coefficient is NLT 0.999.

The mean relative response factors for each concentration level are between 97.0% and 103.0% relative to the L6 level.

The y-intercept is NMT 5.0% of area in 100% level.

E. Accuracy

The dissolution working concentration is 277.8 µg/mL. The accuracy study is conducted to cover a range from 50% to 120% of the dissolution standard concentration.

1. Citrulline Standard Solution

Prepare the standard solution using the same procedure as described herein in the procedure for the dissolution test for Citrulline chewable tablets. The Accuracy study is conducted at three concentration levels. Three samples are prepared in each level.

2. Preparation of the 50% Accuracy Samples

Prepare three A1 (50%) solutions. Weigh accurately about 250 mg of Citrulline reference and 700 mg of placebo into a 1,000-mL dissolution vessel. Add 900 mL of dissolution medium. Prepare the sample solution in the same procedure as the preparation of a single point dissolution sample described in the procedure for the dissolution test for Citrulline chewable tablets.

3. Preparation of the 100% Accuracy Samples

Prepare three A2 (100%) solutions. Weigh accurately about 500 mg of Citrulline reference and 165 mg of placebo and mix them well. Then, put them into a 1,000-mL dissolution vessel, add 900 mL of dissolution medium, and prepare the sample solution in the same procedure as the preparation of a single point dissolution sample described in the procedure for the dissolution test for Citrulline chewable tablets.

4. Preparation of the 120% Accuracy Samples

Prepare three A3 (120%) solutions. Weigh accurately about 600 mg of Citrulline reference and 700 mg of placebo into a 1,000-mL dissolution vessel. Add 900 mL of dissolution medium and prepare the sample solution in the same procedure as the preparation of a single point dissolution sample described in the procedure for the dissolution test for Citrulline chewable tablets.

Establish the system suitability as described in the procedure for the dissolution test for Citrulline chewable tablets. Each of the spiked solutions will be injected in duplicate and a procedural control standard should be placed between every six injections and at the end of the sequence.

Validity Criteria:

Meets system suitability requirements.

Inject each recovery solution in duplicate. The % difference between duplicate injections is within ±2%.

The procedural controls meet criteria.

Acceptance Criteria:

The mean recovery at each level shall be 95%-105% of the amount spiked.

F. Precision

1. Repeatability

Perform the dissolution profile test using six individual Citrulline chewable Tablets on three consecutive days. A homogeneous sample solution is prepared using the same procedure as preparation of single point sample solution described in the procedure for the dissolution test for Citrulline chewable tablets. The repeatability precision of the finished products dissolution test procedure is evaluated by performing six dissolution tests from the same lot of the finished product following the sample solution preparation and test procedures described in the procedure for the dissolution test for Citrulline chewable tablets. Analyze the six sample solutions and determine the amount of Citrulline in percent label claim as described in the test method. The precision of the method is determined by calculating the RSD % of mean dissolution percent released results for three days. Establish the system suitability as described in the procedure for the dissolution test for Citrulline chewable tablets. Each of the sample solutions is injected in duplicate and a procedural control standard should be placed between every six injections and at the end of the sequence, Validity Criteria
Meet system suitability requirements.
The % difference between duplicate injections is within ±2%.
The procedural controls meet criteria.
Acceptance Criteria
All of the 18 sample results are greater than or equal to (Q+5) %.
The RSD of mean dissolution percent for the six tablets on each day should be NMT 5.0%.
The overall RSD of mean dissolution percent for three days should be NMT 5.0%

2. Intermediate Precision

The intermediate precision of the finished products dissolution test procedure is evaluated by performing six dissolution tests from the same lot of the finished products used in the "Repeatability" following the sample solution preparation and test procedures described in this protocol. The intermediate precision should be conducted independently by another analyst, using a different HPLC system, a different column and on a different day. Establish the system suitability as described in the procedure for the dissolution test for Citrulline chewable tablets. Each of the sample solutions is injected in duplicate and a procedural control standard should be placed between every six injections and at the end of the sequence.

Validity Criteria
Meet system suitability requirements.
The % difference between duplicate injections is within ±2%.
The procedural controls meet criteria.
Acceptance Criteria
All of the 6 sample results are greater than or equal to (Q+5) %.
The difference in the mean value between the dissolution results at any two conditions using the same strength does not exceed an absolute 10% at time points with less than 85% dissolved and does exceed 5% for time points above 85%.

G. Standard and Sample Solution Stability

Prepare standard solution using the same procedure as described in ARD-FPTM031C. Prepare sample solution by the following steps. Place a Citrulline Tablet into a 1,000-mL dissolution vessel, add 900-mL of dissolution medium, and prepare the sample solution in the same procedure as preparation of single point sample solution described herein in the procedure for the dissolution test for Citrulline chewable tablets. Establish the system suitability as described in the procedure for the dissolution test for Citrulline chewable tablets. The standard solution and sample solution is stored at room temperature. Inject the sample solution every hour over the course of 48 hours and determine if any significant trend could be observed.

Validity Criteria:
Meets the system suitability requirements.
The procedural controls meet criteria.
Acceptance Criteria:
The standard and the sample solutions are considered stable if the results at each time point are within ±2% of the initial results and no significant trends are observed.

H. Filtration Study

1. Preparation of Dissolution Sample

Run a single chewable tablet dissolution using the conditions specified in the procedure for the dissolution test for Citrulline chewable tablets except proceed directly to an infinity time point (200 RPM for 45 minutes). Stop the paddles from rotating and wait 10 minutes for the undissolved particles to settle. Withdraw a 6-10 mL portion of the solution as described under the procedure for the dissolution test for Citrulline chewable tablets and combine in a suitable container. Place three aliquots of about 10 mL into three 15-mL centrifuge tubes and spin at 2,500 to 3,500 RPM for 5 minutes. Pipette about 7 mL aliquot of the supernate from each centrifuge tube into a suitable container. Divide the remaining solution into three aliquots of about 10 mL each and filter through a 0.45 µm Agilent Regenerated Cellulose Filter discarding the initial 3 mL (one filter for each syringe), and proceed as directed in the sample preparation of the procedure for the dissolution test for Citrulline chewable tablets.

2. Preparation of Standard Solution

Prepare a standard solution for the filtration study following the standard preparation procedure in the procedure for the dissolution test for Citrulline chewable tablets outlined herein. Using 3-10 mL disposable plastic syringes withdraw 3-10 mL aliquots from the working standard solution. Filter each sample solution through a 0.45 µm Agilent Regenerated Cellulose Filter discarding the initial 3 mL (one filter for each syringe), and collect the filtrate in a suitable container. Fill three suitable containers with unfiltered working standard.

3. Preparation of Filter Blanks

Using 3-10 mL disposable plastic syringe withdraw 3-10 mL aliquots of medium. Filter each solution through a 0.45 µm Agilent Regenerated Cellulose Filter discarding the initial 3 mL (one filter for each syringe), and collect the filtrate in a suitable container.

4. Procedure

Read the filtered medium blanks, the filtered standard fractions, the unfiltered standards, the filtered sample fractions, and the centrifuged sample fractions as described in the procedure for the dissolution test for Citrulline chewable tablets in triplicate. Calculate any peak area from the dissolution medium filter blanks as the percentage of the average absorption from the unfiltered standard solution. Calculate the percent difference between the average absorbances of the unfiltered standards and the filtered standards. Calculate the percent difference between the average absorbances of the centrifuged samples and the filtered samples.

Validity Criteria:
Meets the system suitability requirements.
Acceptance Criteria:
The data is evaluated for trends due to the filtration. The difference between the result of filtered solution specified in method and the result of the unfiltered or centrifuged solution should NMT ±2%. If a clear end is observed, adequate filtrate is discarded to assure there is no interference.

I. Robustness Study

It is a measure of the method's capability to remain unaffected by small but deliberate variations in method parameters. The following parameters are independently varied in this study: pH, volume, agitation rate, and temperature of the dissolution medium, wavelength of spectrophotometry.

1. Preparation of the Standard Solution

Prepare a working standard as described herein in the procedure for the dissolution test for Citrulline chewable tablets.

2. pH Variations

The pH is varied by ±0.2 units. The method specified medium is water with pH of 7.0. The varied pH of medium will be prepared as following: dissolve 47.2 g of monobasic Potassium Phosphate, 7.0 g of hydroxide sodium in 7,000 mL of degassed water. Adjust with 1 N sodium hydroxide or diluted phosphoric acid to a pH of 7.2 or 6.8, and mix.

3. Temperature Variations

The temperature is varied by ±2° C. The method dissolution temperature of 37° C. and the varied column temperatures of 39° C. and 35° C. are evaluated.

4. Volume Variations

The volume is varied by about ±10 mL. The method dissolution volume is 900 mL, and the varied volumes are 890 mL and 910 mL.

5. Agitation Rate Variations

The agitation rate is varied by about ±2 rpm. The method agitation rate is 75 rpm, and the varied agitation rates are 73 rpm and 77 rpm.

6. Wavelength Variations:

The wavelength is varied by about ±2 nm. The method wavelength is 200 nm, and the varied agitation rates are 202 nm and 198 nm.

7. Procedure

Run the single point dissolution test using six tablets. Read the Dissolution Working Sample Solution, as described herein in the procedure for the dissolution test for Citrulline chewable tablets. Repeat this sequence for the ten varied conditions. Calculate the percent released of Citrulline for each condition using the average absorbance from the system suitability standards for that condition.

Validity Criteria:

Meets the system suitability requirements.

Acceptance Criteria

The percent Citrulline released in the preparation is Q+5% for each of the varied parameters. The difference in the mean value between the dissolution results at specified parameters and any varied parameters using the same strength does not exceed an absolute 5%.

J. Range

The range of the assay test method is determined by the linearity and accuracy.

Validity Criteria

Meet system suitability requirements.

The data is evaluated for trends due to the extraction. In general, if no trend is observed in the various samples, sonicate with occasional shaking for 5 minutes to extract Citrulline. If a clear trend is observed, extraction for adequate time is conducted to assure there is no interference.

Acceptance Criteria

The mean recovery of the sample sonicated for administered extracting time is within ±2.0% from the recovery of the sample sonicated for the time of the time point next to it.

K. Conclusions

The method shall be considered validated if specificity, accuracy, linearity, precision, robustness, filtration, extraction, and range results meet predefined validity & acceptance criteria.

V. Method of Determination of Related Substances/Degradation Products of Citrulline Chewable Tablets, 500 mg The objective of this example is to define the procedure to determine related substances/degradation products in Citrulline Chewable Tablets (500 mg). The following is a brief listing and summary of parameters of the method.

A. Method

The methods of determination include the Gradient Method, the External Standard, the FLD Detection, and the Quantitation by Peak Area.

B. Equipment

The equipment used in the method includes:
HPLC with variable Fluorometry detector, auto injector, and suitable data processor/recorder;
one pump for reagent transport;
a reaction coil with thermostat: a column 0.25 μm (inside diameter) and 5 m in length;
an analytical balance;
an ultrasonic bath; and
a Regenerated Cellulose Membrane Filter-Agilent.

C. Test Articles

Citrulline RS (reference standard);
Ornithine RS (reference standard);
Arginine RS (SIGMA);
Anhydrous sodium sulfate, AR;
Sodium l-heptane sulfonate, HPLC grade;
Acetic acid, AR;
Boric acid, AR;
2-mercaptoethanol, AR;
Potassium chloride, AR;
Sodium hydroxide, AR;
O-phthalaldehyde, AR;
Ethanol, AR;
Methanol, HPLC grade; and
Purified Water, graded suitable for chromatographic system D. Chromatographic System/Conditions 1. Column: Type: AQCl8
Dimensions: 4.6 mm (i.d.)×25 cm
Particle Size: 5.0 μm
Temperature: 20° C.

2. Diluent: water

3. Detector: Fluorometry (excitation wavelength: 340 nm, detection wavelength: 450 nm), GAIN: 8.

4. Mobile phase:

| Flow Rate: | 0.8 mL/min |
|---|---|
| Total Run Time: | 60 minutes |
| Solution A: | Dissolve 28.4 g of anhydrous sodium sulfate and 5.2 g sodium l-heptane sulfonate in 1,000 mL of water. Add 1 mL of acetic acid, and mix well. Filter and degas. |
| Solution B: | Methanol |
| Mobile phase A: | Solution A |
| Mobile phase B: | Filter and degas a mixture of Solution A and Solution B at 80:20 ratio. |

The chromatograph is programmed as follows:

| Time (minutes) | Solution A (%) | Solution B (%) | Flow Rate (mL/min) |
|---|---|---|---|
| 0 | 100 | 0 | 0.8 |
| 6 | 100 | 0 | 0.8 |
| 8 | 0 | 100 | 0.8 |
| 40 | 0 | 100 | 0.8 |

| Time (minutes) | Solution A (%) | Solution B (%) | Flow Rate (mL/min) |
| --- | --- | --- | --- |
| 41 | 100 | 0 | 0.8 |
| 50 | 100 | 0 | 0.8 |

Note: keep the ratio of the mobile phase solution constant when preparing the mobile phase.

5. Reagent: Dissolve 6.2 g boric acid, 7.4 g potassium chloride, 3.5 g sodium hydroxide in 1,000 mL of water. Add 10 mL of a solution of o-phthalaldehyde in ethanol (4 g in 25 mL) and 4 mL of 2-mercaptoethanol.
6. Reaction temperature: A constant temperature of 40° C.
7. Flow rate of the reagent: 0.5 mL per minute.

E. Standard Solution Preparation

Weigh out accurately about 100.0 mg of Citrulline RS, transfer into a 100-mL volumetric flask. Dissolve and dilute to volume with diluent to obtain a solution having a known concentration of about 1,000 μg/mL. Pipette 1.0 mL of the solution into a 200-mL volumetric flask. Dilute to volume with diluent and mix well. The concentration of Citrulline is about 5.0 μg/mL. The resulting solution will be referred to as std. in this section.

F. Resolution Solution Preparation (SS)

Weigh out accurately about 10.0 mg of Citrulline RS and 10.0 mg Ornithine RS into a 100-mL volumetric flask. Dissolve and dilute to volume with diluent. Mix well to obtain a solution having a known concentration of about 100 μg/mL. This solution is the system suitability solution.

G. System Suitability Test
1. Inject 10 μL of mobile phase. Inject 10 μL of diluent. Check baseline noise and drift or any other sign of system instability. Repeat injections if necessary until the system is stable. Note retention time of any solvent related peaks.
2. Inject 10 μL of the system suitability solution.
3. Compare the retention time (RT) to the typical RT. The typical values are as follows:

|  | Approx. RT (min) |
| --- | --- |
| Citrulline | 5.0 ± 1.0 min |
| Ornithine | 7.0 ± 1.0 min |

Take appropriate action if a significant deviation from typical values is noted.

4. Calculate the following resolution factor (R). Take appropriate action if R (between Compactin and Citrulline) is less than 5.0.
5. Calculate the column efficiency (N) using Citrulline peak. Take appropriate action if the number of theoretical plates is less than 3,000.
6. Consecutively inject six 10 μL of std.
7. Calculate the mean and relative standard deviation (RSD) of Citrulline peak area from six injections of std.
8. Take appropriate action if an RSD of more than 5.0% is found.

H. Sample Solution (Spl)
1. Weigh 20 tablets and grind into a fine homogenous powder. Transfer an accurately weighed portion of the powder, equivalent to about 100 mg of Citrulline into a 100-mL volumetric flask.
2. Add about 50 mL of water and sonicate with occasional shaking for 15 minutes. Allow the solution to equilibrate to room temperature and then dilute to volume with water and mix well. Pass the solution through a 0.45 μm filter membrane, filter a portion into autosampler vials after discarding the first 5 mL of the filtrate.

I. Quantitation
1. For quantitation, use the results of six consecutive injections of std. If calibration is performed just prior to sample injections, these result may be used.
2. Inject two 10 μL of the sample solution preparation (spl).
3. Inject 10 μL of the standard solution every 6-12 injections to check the retention time and the peak area of Citrulline. If a deviation of more than 5.0% is found when compared to the average of six system suitability injections, conduct the system suitability test again ensuring there is no carry-over from previous injections and the system is stable.

J. Calculation
1. Quantitate known related substances using the 0.5% Citrulline standard and the appropriate response factor. The list below indicates these compounds, their retention times (RT), their relative retention (RRT) based on an RT of 5.0 minutes for Citrulline, and their relative response factors (F).

| Compound | Approx. RT (min) | RRT | F |
| --- | --- | --- | --- |
| Citrulline | 5.0 | / | / |
| Ornithine | 7.2 | 1.4 | 2.7 |
| Arginine | 18.0 | 3.6 | 1.0 |

$$\text{Related Substance} = \frac{A_{spl.} \times F \times W_{std.}/100 \text{ mL} \times 1.0 \text{ mL}/200 \text{ mL} \times P \times 100}{A_{std.} \times W_{spl.}/100 \text{ mL} \times LC/Wa}$$

Where:

$A_{Std.}$=Mean of peak area of Citrulline in the std chromatograms $A_{Spl.}$=Peak area of the related compound in the sample solution chromatogram $W_{Std.}$=Weight of the Citrulline Reference Standard of std., in mg $W_{Spl.}$=Weight of the Citrulline tablet powder, in mg F=Relative Response factor P=Purity factor for the Citrulline Reference Standard LC=Label claim of Citrulline, in mg/tablet Wa=Mean content of 20 Citrulline Chewable Tablets, in mg 2. Calculation the total related substances and degradation products present, in percent using the following expression:

Ornithine %+Arginine %+Unknown−Imp.a%+Imp.b%+Imp.c% . . . +Unknown N%=Total impurities %

VI. Validation Protocols for the Determination of Related Substances/Degradation Products of Citrulline Chewable Tablets, 500 mg The objective of this example is to describe the protocol to validate and demonstrate the suitability of test procedures described in the test method herein above for the product of Citrulline chewable tablets (500 mg). The protocol is similar to the protocol to validate and demonstrate the suitability of the test method of determination of related substances and degradation products of Citrulline API described above. Therefore, the protocol is not described in detail herein.

Summarily, the example protocol validates a Stability Indicating assay method for the quantitation of related compounds employing post column derive method with High Performance Liquid Chromatography (HPLC) with FLD detection. The suitable Excitation wavelength for the detection of Citrulline and its related compounds is 340 nm and the Detection wavelength is 450 nm. PMT-Gain is 8. The validation of the method is accomplished by following USP/NF current guidelines. The protocol describes in detail the proposed experiments and acceptance criteria for the validation of the method.

The test method is used to determine two known related compounds as well as individual and unspecified related compounds. The following studies are conducted to make sure that the method is suitable for testing 500 mg of Citrulline chewable tablets: system suitability, specificity (sample matrix interference, known impurities interference and stability-indicating studies), standard linearity, accuracy, range, precision (repeatability), intermediate precision (ruggedness), limit of detection (LOD)/limit of quantitation (LOQ), standard and sample solutions stability, robustness and filtration study. All the tests listed above are conducted following the impurities analytical method outlined herein. USP-current, EP (Fifth Edition and supplements), ICH guidelines are used as references. The method shall be considered validated and suitable if specificity, accuracy, linearity, precision, robustness, filtration and range results meet predefined validity & acceptance criteria.

Embodiments of the present disclosure shown in the drawings and described above are exemplary of numerous embodiments that can be made within the scope of the appending claims. The configurations described herein can comprise numerous configurations other than those specifically disclosed.

What is claimed is:

1. A process for producing a suitable purity grade of L-Citrulline, the process comprising:
   contacting crude L-Citrulline in an aqueous solution with activated carbon at a temperature above approximately 50° C. and below the temperature of denaturement for the L-Citrulline for an interval sufficient to remove at least one contaminant from the L-Citrulline; and
   concentrating the dissolved L-Citrulline relative to the aqueous solution by initially removing the activated carbon from contact with the aqueous solution and, after removing the activated carbon, concentrating the resulting solution at an elevated temperature for an interval sufficient to achieve at least a 3:1 concentration ratio.

2. The process of claim 1, further comprising crystallizing the L-Citrulline present in the concentrated liquid.

3. The process of claim 2, wherein the crystallizing step comprises:
   diluting the concentrated liquid with at least an equal portion of organic liquid;
   depressing the temperature of the resulting liquid to a level below about 15°; and
   blending the material for an interval sufficient to accomplish crystal formation of the L-Citrulline.

4. The process of claim 2, further comprising:
   dissolving the L-Citrulline crystals obtained in the step of crystallizing in at least an equal volume of a diluent; and
   contacting the resulting solution with a activated carbon for an interval to remove at least one of discoloration and endotoxin.

5. The process of claim 4, further comprising crystallizing the L-Citrulline by reducing the volume of the added diluent at a temperature less than about 15° C. and permitting crystal formation of the L-Citrulline.

6. The process of claim 5, wherein the resulting crystals are dissolved in a suitable diluent at a volume of at least twice the volume of the resulting L-Citrulline crystals and the resulting solution is subjected to filtration and concentration.

7. The process of claim 4, wherein the contacting step occurs at a temperature between about 50° C. and about 70° C.

8. The process of claim 1, further comprising harvesting L-Citrulline crystals from the concentrated solution after cooling to a solution temperature less than 15° C.

9. The process of claim 1, wherein the crude L-Citrulline solution is obtained from microbial conversion of arginine.

10. The method of claim 1 wherein the crude L-Citrulline in an aqueous solution is obtained by the steps of dissolving arginine into an aqueous solution to obtain a conversion solution and inoculating the conversion solution with a microbial strain of streptoccic thalli and incubating the inoculated conversion solution for an interval sufficient to produce crude L-Citrulline and wherein the method further comprises the step of crystalizing the L-Citrulline present in the concentrated liquid and integrating the resulting crystals into one of: an oral dose, a chewable composition, a granular composition, an injectable solution.

* * * * *